(12) United States Patent
Liu et al.

(10) Patent No.: US 11,175,204 B1
(45) Date of Patent: Nov. 16, 2021

(54) 7-HYDROXYCOUMARIN-BASED CELL-TRACKING REAGENTS

(71) Applicant: LIFE TECHNOLOGIES CORPORATION, Carlsbad, CA (US)

(72) Inventors: Jixiang Liu, Santa Clara, CA (US); Hee Chol Kang, Eugene, OR (US); Kyle Gee, Springfield, OR (US); Christopher Langsdorf, Eugene, OR (US); Jolene Bradford, Eugene, OR (US); Gayle Buller, Springfield, OR (US)

(73) Assignee: Life Technologies Corporation, Carlsbad, CA (US)

( * ) Notice: Subject to any disclaimer, the term of this patent is extended or adjusted under 35 U.S.C. 154(b) by 1020 days.

(21) Appl. No.: 15/192,107

(22) Filed: Jun. 24, 2016

Related U.S. Application Data

(60) Division of application No. 14/801,000, filed on Jul. 16, 2015, now Pat. No. 9,400,273, which is a continuation of application No. 12/962,898, filed on Dec. 8, 2010, now abandoned.

(60) Provisional application No. 61/267,953, filed on Dec. 9, 2009, provisional application No. 61/295,371, filed on Jan. 15, 2010.

(51) Int. Cl.
| | |
|---|---|
| *C07D 311/00* | (2006.01) |
| *G01N 1/30* | (2006.01) |
| *C07D 405/12* | (2006.01) |
| *C07D 405/14* | (2006.01) |
| *G01N 33/50* | (2006.01) |

(52) U.S. Cl.
CPC ............ *G01N 1/30* (2013.01); *C07D 405/12* (2013.01); *C07D 405/14* (2013.01); *G01N 33/5005* (2013.01); *G01N 33/5097* (2013.01); *G01N 2001/302* (2013.01)

(58) Field of Classification Search
CPC .............................. G01N 33/5008; G01N 1/30
USPC ............................................ 435/29; 549/399
See application file for complete search history.

(56) References Cited

U.S. PATENT DOCUMENTS

| | | | |
|---|---|---|---|
| 4,279,992 A | 7/1981 | Boguslaski | |
| 5,830,912 A | 11/1998 | Gee et al. | |
| 5,880,131 A * | 3/1999 | Greenwald | C07D 305/14 514/279 |
| 6,200,762 B1 | 3/2001 | Zlokarnik et al. | |
| 6,291,162 B1 | 9/2001 | Tsien et al. | |
| 6,596,522 B2 | 7/2003 | Tsien et al. | |
| 7,304,168 B2 | 12/2007 | Li et al. | |
| 8,431,416 B2 | 4/2013 | Diwu et al. | |
| 2010/0029017 A1 * | 2/2010 | Diwu | G01N 33/533 436/536 |

FOREIGN PATENT DOCUMENTS

| | | |
|---|---|---|
| WO | WO 2008/145830 | 12/2008 |
| WO | WO 2009/067031 | 5/2009 |

OTHER PUBLICATIONS

Orange et al. Chemical Communications (Cambridge, United Kingdom)(2008), (10), 1217-1219.*
Parish, Immunology and Cell Biology 1999, 77, 499-508.*
Abrams, B. et al., "3-Carboxy-6-chloro-7-hydroxycoumarin: A highly fluorescent, water-soluble violet-excitable dye for cell analysis", *Anal. Biochem.*, vol. 386, 2009, pp. 262-269.
Bercovici, N. et al., "Multiparameter precursor analysis of T-cell responses to antigen", *J. Immunol. Methods*, vol. 276, 2003, pp. 5-17.
Brinkley, "A Brief Survey of Methods for Preparing Protein Conjugates with Dyes, Haptens, and Cross-Linking Reagents", *Bioconjugate Chemistry*, vol. 3, No. 1, 1992, 2-13.
Chakravarti, D. et al., "Synthesis of Coumarins from Phenols and B-Ketonic Esters. Part IV. Coumarins from 4-Chloro- and 2-Nitroresorcins", *J. Indian Chem. Soc.*, University College of Science and Technology, Calcutta, 1935, pp. 622-626.
Fazekas De St Groth, B. et al., "Carboxyfluorescein diacetate succinimidyl ester and the virgin lymphocyte: A marriage made in heaven", *Immunol. Cell Biol.*, vol. 77, 1999, pp. 530-538.
Grandl, J. et al., "Fluorescent Epibatidine Agonists for Neuronal and Muscle-Type Nicotinic Acetylcholine Receptors", *Angewandte Chemie*, International Edition, 2007, 3505-2508.
Gutierrez, M. et al., "The first fiuorogenic assay for detecting a Baeyer-Villigerase activity in microbial cells", *Org. Biomol. Chem.*, vol. 1, 2003, pp. 3500-3506.
Haugland, Richard P., "Molecular Probes Handbook of Fluorescent Probes and Research Chemicals", *Molecular Probes, Inc.*, Sets 1-7, 1992, pp. 9-41.
Haugland, Rosaria P., "Coupling of monoclonal antibodies with fluorophores", *Methods in Molecular Biology*, Monoclonal Antibody Protocols, vol. 45, 1995, pp. 205-243.
Hawkins, Edwin et al., "Measuring lymphocyte proliferation, survival and differentiation using CFSE time-series", *Nat. Protoc.*, vol. 2, 2007, pp. 2057-2067.
Lyons, A. B. et al., "Flow Cytometric Analysis of Cell Division by Dye Dilution", *Current Protocols in Cytometry*, Supp. 27, 2004, pp. 9.11.1-9.11.10.
Orange, C. et al., "Synthesis and photochemical properties of a light-activated fluorophore to label His-tagged proteins", *Chem. Commun.*, 2008, 1217-1219.
Parish, Christopher R., "Fluorescent dyes for lymphocyte migration and proliferation studies", *Immunology and Cell Biology*, vol. 77, 1999, pp. 499-508.
Sun, Wei-Chuan et al., "Synthesis of novel fluorinated coumarins: Excellent UV-light excitable fluorescent dyes", *Bioorg and Med Chem Letters*, vol. 8, No. 22, 1998, pp. 3107-3110.

(Continued)

*Primary Examiner* — Nizal S Chandrakumar

(57) ABSTRACT

Described herein are compounds, methods, and kits for long-term tracking of cell proliferation, differentiation, and/or function. The compounds of the present invention are novel cell-tracking reagents, efficiently excitable with a 405-nm violet laser, that provide bright fluorescence intensity, uniform cell staining, and good retention within cells as well as low toxicity toward cells.

6 Claims, 18 Drawing Sheets

(56) References Cited

OTHER PUBLICATIONS

Wallace, Paul K. et al., "Tracking Antigen-Driven Responses by Flow Cytometry: Monitoring Proliferation by Dye Dilution", *Cytometry Part A*, vol. 73A, 2008, pp. 1019-1034.

Wolff, C. et al., "Comparative Study of Membrane Potential-Sensitive Fluorescent Probes and their Use in Ion Channel Screening Assays", *J Biomol Screen*, 8, 2003, 533-543.

www.invitrogen.com, , "The Flow Cytometry Violet Laser Resource Guide", *Molecular Probes violet laser—excitable reagents*. 2012, 1-16.

Zhao, Y. et al., "New Caged Coumarin Fluorophores with Extraordinary Uncaging Cross Sections Suitable for Biological Imaging Applications", *J. Am. Chem. Soc.*, vol. 126, 2004, 4653-4663.

\* cited by examiner

5µM Compound Violet

Cellular Lights™ Talin-GFP

Cellular Lights™ Talin-GFP And 5µM Compound Violet

Proposed Experimental Protocol for Compound Violet Cell Proliferation Kit

Experimental Protocol

1. Bring a vial of Compound Violet to room temperature.
2. Add 20μL anhydrous DMSO to prepare a 5mM stock solution.
3. Add 1μL of stock solution to 1mL cells for a final concentration of 5μM.
4. Incubate 20 minutes.
5. Quench and wash.
6. Proceed with stimulation and analysis.

7-HYDROXYCOUMARIN-BASED CELL-TRACKING REAGENTS

CROSS REFERENCE TO RELATED APPLICATIONS

This application is a Divisional application of U.S. application Ser. No. 14/801,000, filed Jul. 16, 2015, which is a Continuation of U.S. application Ser. No. 12/962,898, filed Dec. 8, 2010, which claims the benefit of U.S. Ser. No. 61/267,953, filed Dec. 9, 2009, and U.S. Ser. No. 61/295,371, filed Jan. 15, 2010, the disclosures of which are hereby incorporated herein by reference in their entirety.

FIELD OF THE INVENTION

The present invention relates to 7-hydroxycoumarin-based fluorophores, including chemically-reactive fluorophores and conjugates of such fluorophores, as well as uses of such fluorophores as cell-tracking reagents.

BACKGROUND OF THE INVENTION

Methods for monitoring cell proliferation, differentiation, and function using flow cytometry have enabled investigation of complex biological phenomena, e.g., immune responses to antigen, which responses involve complex interactions among multiple cell types (see, Wallace P K, Tario J D, Jr., Fisher J L, Wallace S S, Ernstoff M S, Muirhead K A. Tracking Antigen-Driven Responses by Flow Cytometry: Monitoring Proliferation by Dye Dilution. *Cytometry Part A* 73A: 1019-1034, 2008). So called cell-tracking dyes have proven useful for qualitative and quantitative monitoring of cell division, both in vivo and in vitro (see, Hawkins E D, Hommel M, Turner M L, Battye F L, Markham J F, Hodgkin P D. Measuring lymphocyte proliferation, survival and differentiation using CFSE time-series data. *Nat Protoc* 2007, 2:2057-2067; and Wallace P K, Muirhead K A. Cell tracking 2007: A proliferation of probes and applications. *Immunol Invest* 2007, 36:527-561). These dyes, also referred to herein as cell-tracking reagents which term is inclusive of cell-tracing reagents, generate a fluorescent signal that, while relatively stable in non-dividing cells, progressively decreases with each round of cell division. Reduction in fluorescence intensity can be quantified by flow cytometry in conjunction with any of several different algorithms to estimate the extent of proliferation (in response to a particular stimulus) based on dye dilution (see, Wallace et al., *Cytometry Part A* 73A: 1019-1034, 2008). A major advantage of using flow cytometry in conjunction with cell-tracking reagents to monitor the extent of cell division is that cells can also be stained for expression of other cell surface or intracellular markers to define lineage, functionality, activation state, cytokine expression, etc. (see. Bercovici N, Givan A L, Waugh M G, Fisher J L, Vernel-Pauillac F, Ernstoff M S, Abastado J P, Wallace P K. Multiparameter precursor analysis of T-cell responses to antigen. *J Immunol Methods* 2003, 276:5-17; Fazekas de St Groth B, Smith A L, Koh W P, Girgis L, Cook M C, Bertolino P. Carboxyfluorescein diacetate succinimidyl ester and the virgin lymphocyte: A marriage made in heaven. *Immunol Cell Biol* 1999, 77:530-538; and Tanaka Y, Ohdan H, Onoe T, Asahara T. Multiparameter flow cytometric approach for simultaneous evaluation of proliferation and cytokine-secreting activity in T cells responding to allo-stimulation. *Immunol Invest* 2004, 33:309-324).

Carboxyfluorescein diacetate succinimidyl ester (CFDA-SE, or, alternatively, ME) remains a popular, commercially available cell-tracking reagent, excitable with 488-nm laser light to give a bright green fluorescence In combination with another cell-tracking reagent, i.e., the 647 nm-excitable red-fluorescent lipophilic membrane dye PKH26, CFDA-SE has been widely used to monitor cell proliferation by flow cytometry in heterogeneous cell populations. Both reagents stain cells with a bright homogeneous fluorescence, which is partitioned between daughter cells during each cell division.

Notwithstanding the current popularity of CFDA-SE, there remains a need for alternative fluorescent dyes, useful as cell-tracking reagents, with different spectral properties. Such reagents may be combined for simultaneous use not only with CFDA-SE, but also with other currently-available cell-tracking reagents, such as, for example, the 488 nm-excitable reagent Green Fluorescent Protein (GFP), or with the 647 nm-excitable red-emitting dye PKH26. Such use thereby permitting researchers to study cell proliferation, differentiation, and/or function in otherwise indistinguishable cell populations in mixed cell cultures with multi-color applications using flow cytometry.

Many 7-hydroxycoumarin derivatives have been widely used for labeling biological molecules, e.g., proteins inside cells, due to their favorable fluorescent properties. Sun et al. developed a series of fluorinated 7-hydroxycoumarin analogs and demonstrated them to be highly fluorescent and photostabile (see, Sun W-C, Gee K R, Haugland R P. Synthesis of novel fluorinated coumarins: Excellent UV-light excitable fluorescent dyes. *Bioorg and Med Chem Letters*, 1988, 8, 3107-3110). Such analogs have been used for the preparation of fluorescent protein conjugates as well as substrates for a variety of enzymes, including, but not limited to, phosphatases, β-lactamases, and β-galactosidases. In particular, 3-carboxy-6,8-difluoro-7-hydroxycoumarin (otherwise known as Pacific Blue™ dye) has been broadly employed as a 405 nm violet laser-excitable protein labeling reagent (see, Gee K R, Haugland R P, Sun W-C. Derivatives of 6,8-difluoro-7-hydroxycoumarins. U.S. Pat. No. 5,380,912 (issued Nov. 3, 1998)). More recently and in conjunction with flow cytometry, Abrams et al. described 3-carboxy-6-chloro-7-hydroxycoumarin as a violet laser-excitable protein labeling reagent having a brightness similar to that of Pacific Blue™ dye (see, Abrams B, Diwu Z. Guryev O, Aleshkov S, Hingorani R, Edinger M, Lee R, Link J, Dubrovsky T. 3-Carboxy-6-chloro-7-hydroxycoumarin: A highly fluorescent, water-soluble violet-excitable dye for cell analysis. *Anal Biochem*, 2009, 386, 262-269). However, neither the aforementioned Sun et al. nor Abrams et al. references describe compounds applicable for use as cell-tracking reagents in long-term studies of cell proliferation, differentiation, and/or function.

Recently, CellVue® Lavender has been employed as a new, cell-tracking reagent utilizing 405 nm violet laser light excitation. However, CellVue® Lavender appears to suffer from limitations including, for example, low fluorescence intensity and a broad emission wavelength well above 550 nm, the combination of which makes its use non-ideal in multi-color applications using flow cytometry.

The development of cell-tracking reagents efficiently excitable with a 405 nm violet laser to provide bright fluorescence intensity for long-term monitoring of cell proliferation, differentiation, migration, location, and/or function using flow cytometry has, heretofore, not been realized.

SUMMARY OF THE INVENTION

Described herein are compounds, methods, and kits for long-term tracking of cell proliferation, differentiation, and/ or function. The compounds of the present invention are novel cell-tracking reagents, efficiently excitable with a 405 nm violet laser, that provide bright fluorescence intensity, uniform cell staining, and good retention within cells as well as low toxicity toward cells. These cell-tracking reagents may be used in place of and/or in combination with other currently-available cell-tracking reagents, such as, for example, the 488 nm-excitable reagents CFDA-SE and/or Green Fluorescent Protein (GFP) as well as the 647 nm-excitable red-emitting dye PKH26, to track and/or stain otherwise indistinguishable cell populations in mixed cell cultures via flow cytometry and/or fluorescence microscopy, respectively. In addition, described herein are processes for preparing novel cell-tracking reagents for use in the disclosed methods and kits of the present invention.

One illustrative aspect of the present invention provides a novel cell-tracking reagent (compound) having the structural formula (I):

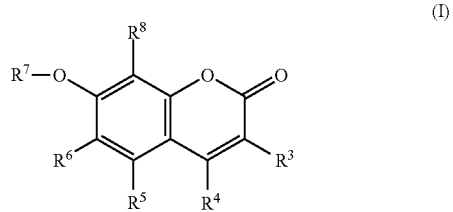

(I)

or a pharmaceutically acceptable salt thereof, wherein
$R^3$ is H, $C_1$-$C_{18}$ alkyl, $C_1$-$C_{18}$ perfluoroalkyl, CN, formyl, aryl, heteroaryl, arylcarbonyl, or —(C=O)—$NR^1R^2$ where $R^1$ and $R^2$ are independently H, $C_1$-$C_6$ alkyl, aryl, or $R^1$ and $R^2$ taken in combination are —(CH$_2$)$_2$-M-(CH$_2$)$_2$— where M is a single bond, —O—, —CH$_2$—, or —$NR^9$—, where $R^9$ is H or $C_1$-$C_6$ alkyl; or $R^3$ is -L-$R_X$ or -L-$S_C$;
$R^4$ is H, OH, CN, $C_1$-$C_{18}$ alkyl, $C_1$-$C_{18}$ perfluoroalkyl, sulfomethyl, biologically compatible salt of sulfomethyl, halomethyl, aryl, -L-$R_X$ or -L-$S_C$;
$R^5$ is H or $C_1$-$C_6$ alkoxy;
$R^6$ is Cl or F;
$R^7$ is H, or a monovalent moiety derived by removal of a hydroxy group from a phosphate, a thiophosphate, a sulfate, or a biologically compatible salt thereof; or a monovalent moiety derived by removal of a hydroxy group from a carboxy group of an aliphatic or aromatic carboxylic acid; or a monovalent moiety derived by removal of a hydroxy group from an alcohol or from a mono- or polysaccharide; or $R^7$ is a photolabile caging group; and
$R^8$ is H, Cl, F, $C_1$-$C_6$ alkoxy or $C_1$-$C_6$ alkyl;
wherein
aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamido;
heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$-$C_6$ alkyl, or $C_1$-$C_6$ alkoxy;
each L is independently a single covalent bond, or L is a covalent linkage having 1-24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds, nitrogen-sulfur bonds, sulfur-oxygen bonds, and carbon-sulfur bonds;
$R_X$ is a reactive group; and
$S_C$ is a conjugated substance;
provided that at least one of $R^3$ and $R^4$ is -L-$R_X$ or -L-$S_C$; and that at least one of $R^6$ and $R^8$ is not F.

Another illustrative aspect of the present invention provides a kit for tracking cell proliferation, differentiation, and/or function, the kit being compatible for use with, for example, flow cytometry and fluorescence microscopy, and including:
a) a novel cell-tracking reagent (compound) described herein;
b) an organic solvent; and
c) a desiccant.

Another illustrative aspect of the present invention provides a method for tracking cell proliferation, differentiation, and/or function, the method being compatible for use with, for example, flow cytometry and fluorescence microscopy, and including the steps of:
a) incubating a mixture of cells and a novel cell-tracking reagent (compound) described herein;
b) providing a stimulus to the mixture to elicit a fluorescent signal; and
c) analyzing the stimulated mixture.

Another illustrative aspect of the present invention provides a process for preparing a novel cell-tracking reagent (compound) of structural formula IIIa or IIIb

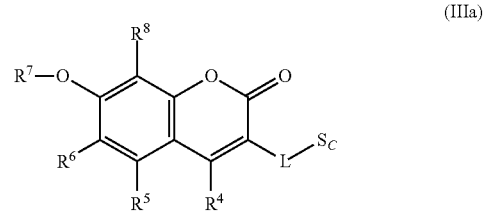

(IIIa)

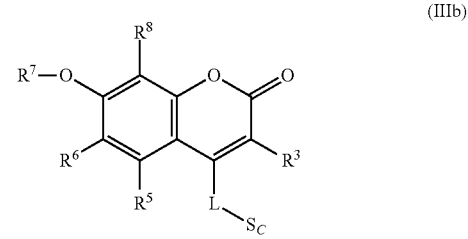

(IIIb)

the process comprising:
a) reacting a novel cell-tracking reagent (compound) of structural formula IIa or IIb, respectively

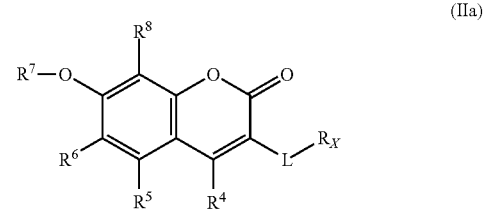

(IIa)

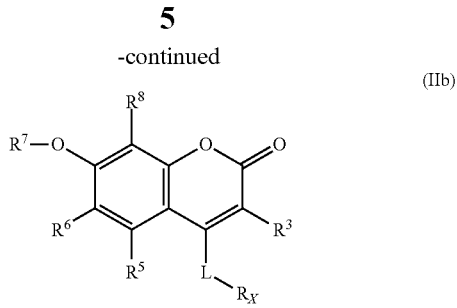

(IIb)

with a substance S to be conjugated thereto, thereby resulting in a conjugated substance $S_C$, wherein:

$R^3$, $R^4$, $R^5$, $R^6$, $R^7$, $R^8$, L, $R_X$, and $S_C$ are as defined herein.

Other illustrative aspects, features and advantages of the present invention will become apparent from the following detailed description. It should be understood, however, that the detailed description and the specific examples that follow, while indicating preferred embodiments of the invention, are given by way of illustration only. It is expected that various changes and modifications within the spirit and scope of the present invention will become apparent to those skilled in the art.

BRIEF DESCRIPTION OF THE FIGURES

FIG. 1 shows the results of Biological Application Example 1:

FIG. 2 shows the results of Biological Application Example 2:

FIG. 3 shows the results of Biological Application Example 3:

FIG. 4 shows the results of Biological Application Example 4:

FIG. 5 shows the results of Biological Application Example 5:

FIG. 5g—3T3-L1 cells stained with 1 μM Compound Violet showing a bright, uniform fluorescence signal immediately after staining.

FIG. 5h-3T3-L1 cells stained with 1 μM Compound Violet showing that the fluorescence signal has decreased substantially after four days of cell division in culture.

DETAILED DESCRIPTION OF THE INVENTION

Figure 1A:
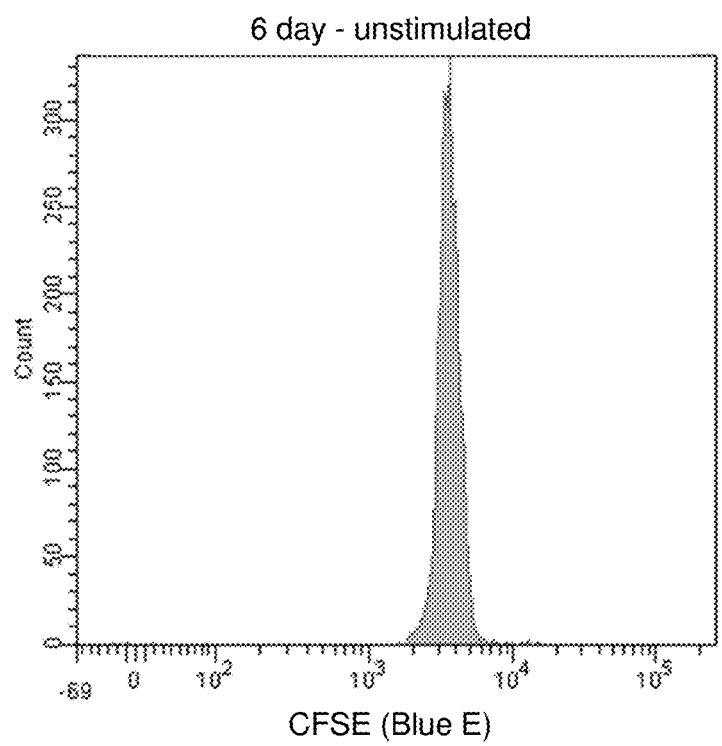
FIG. 1a, 1e, 1i, 1m—Histograms showing fluorescence intensity and coefficient of variation from unstimulated cells six days after staining with CFSE, Compound 2, Compound 6, and Compound 7, respectively (showing little change from initial staining).
Figure 1B:
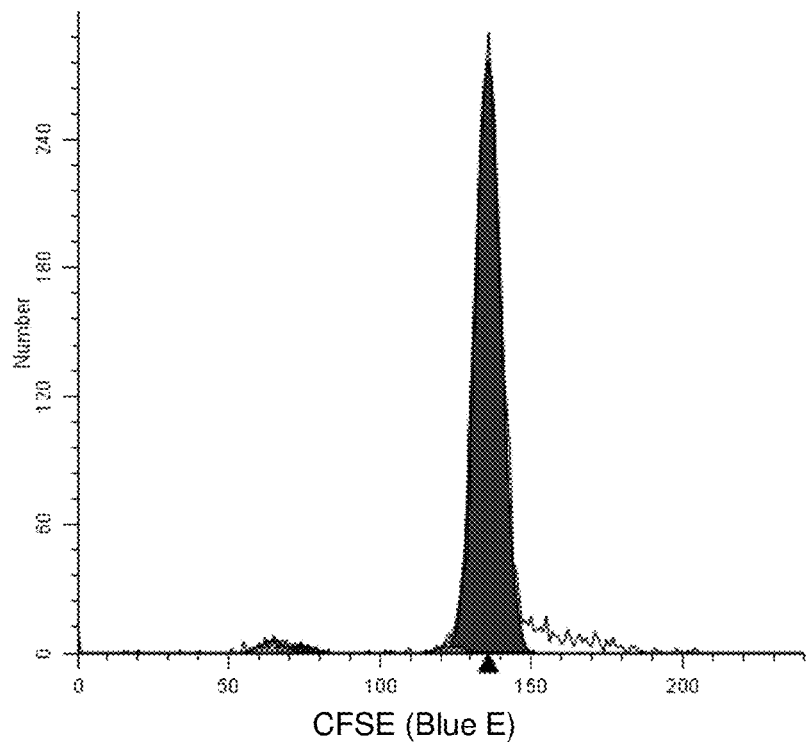
FIG. 1b, 1f, 1j, 1n—Smoothed histograms corresponding to those in FIGS. 1a, 1e, 1i, and 1m, respectively; the high intensity and low coefficient of variation of the fluorescent signal shown in these figures are crucial for accurately tracking cell proliferation.
Figure 1C:
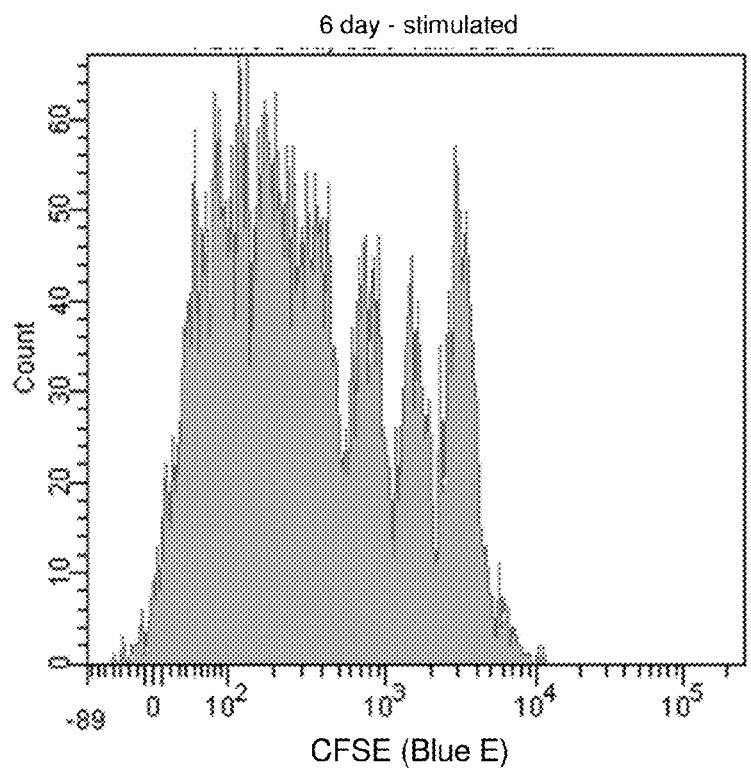
FIG. 1c, 1g, 1k, 1o—Histograms showing fluorescence intensity and coefficient of variation from stimulated cells six days after staining with CFSE, Compound 2, Compound 6, and Compound 7, respectively, revealing distinct peaks corresponding to each generation of cells.
Figure 1D:
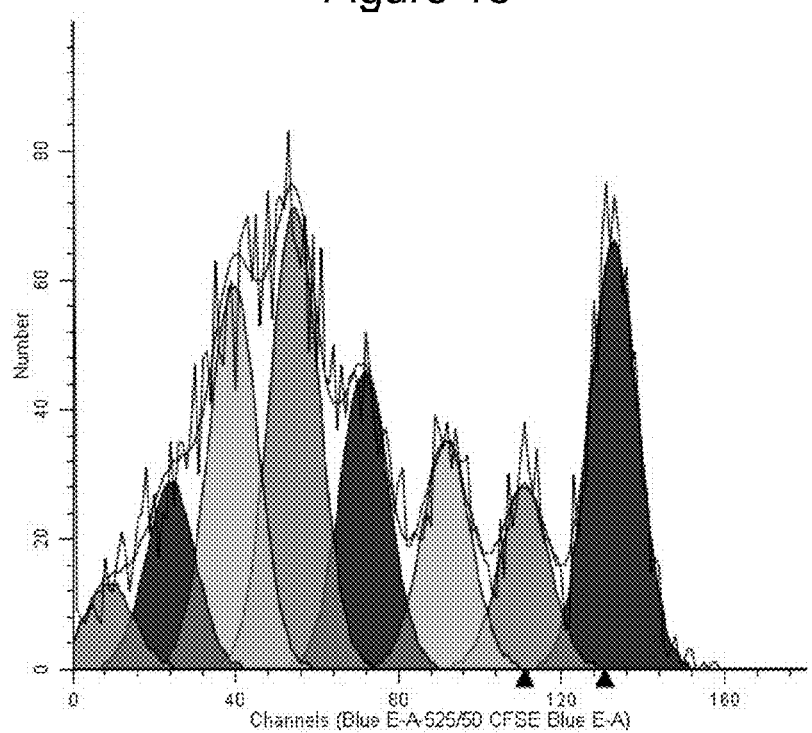
FIG. 1d, 1h, 1l, 1p—Further analysis of histograms from FIGS. 1c, 1g, 1k, and 1o, respectively, with population analysis software (ModFit LT, Verity Software House) revealing more detailed information about the eight generations of cells in Example 1.
Figure 1E:
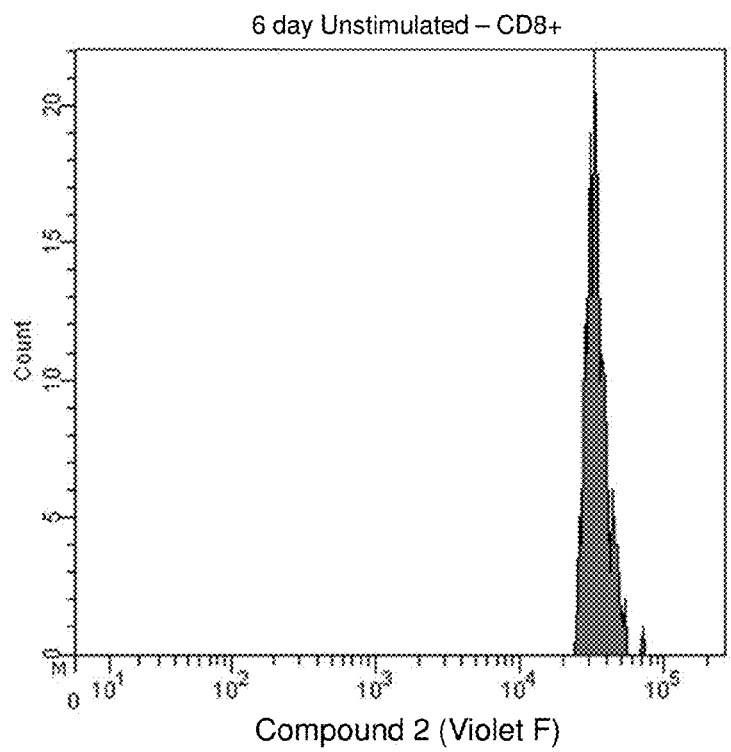
Figure 1F:
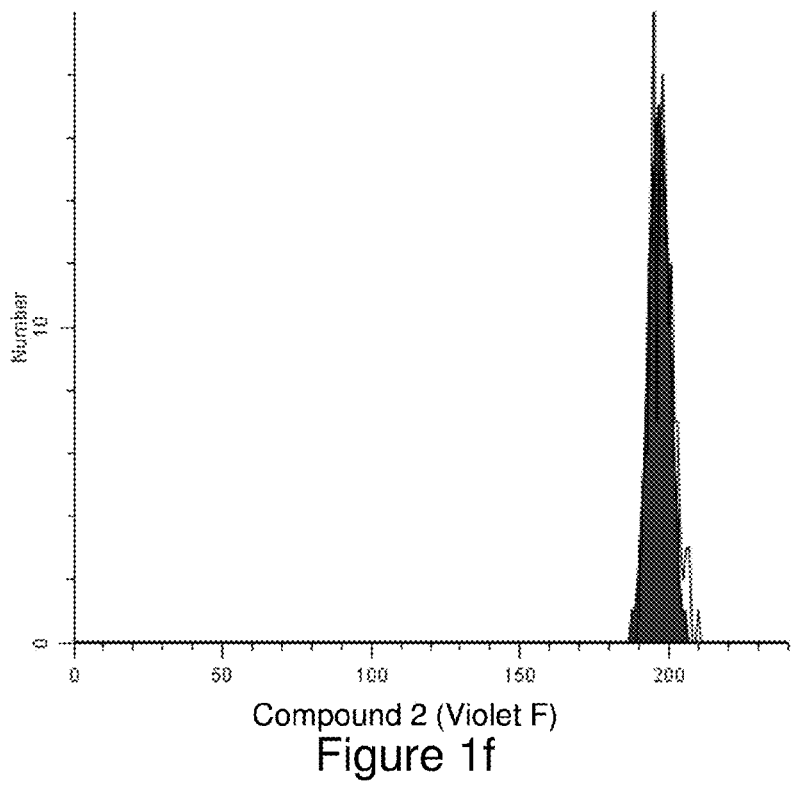
Figure 1G:
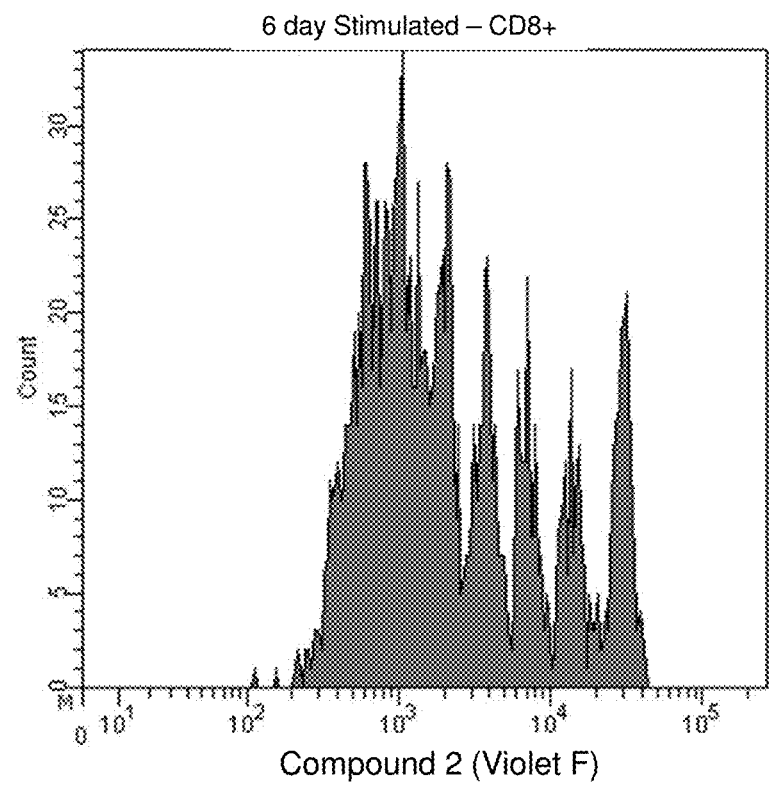
Figure 1H:
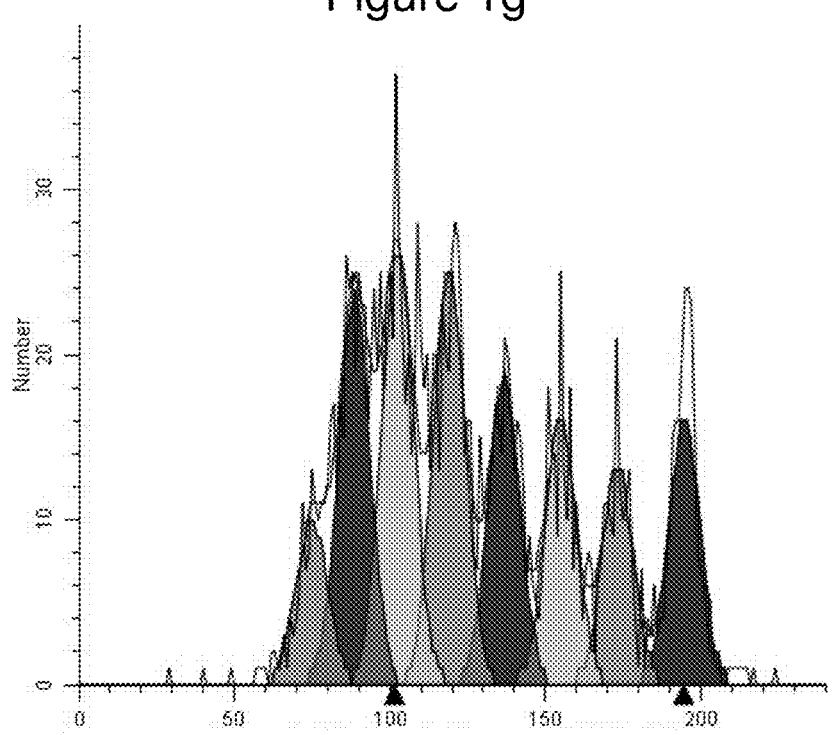
Figure 1I:
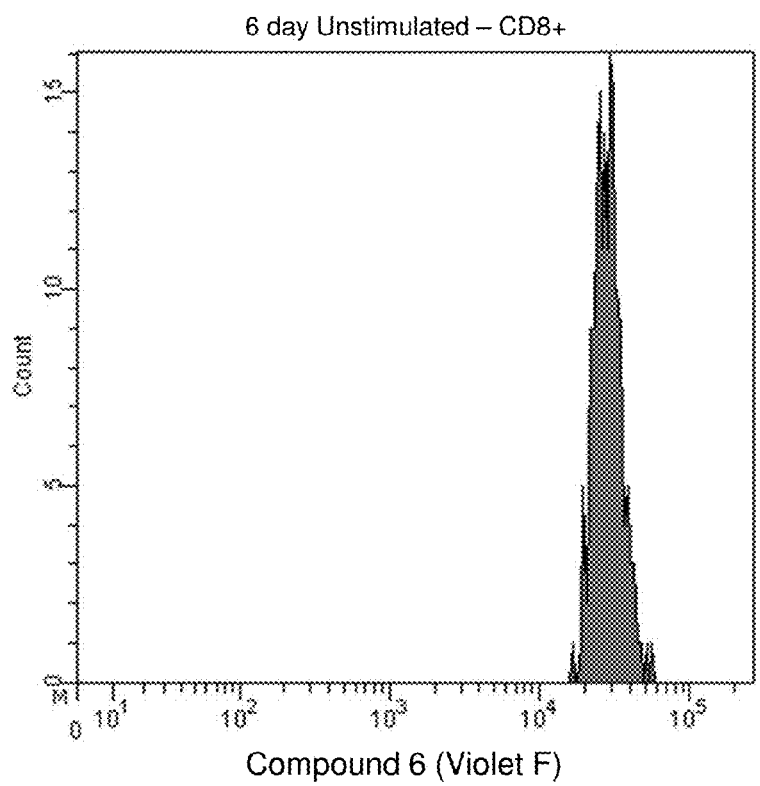
Figure 1J:
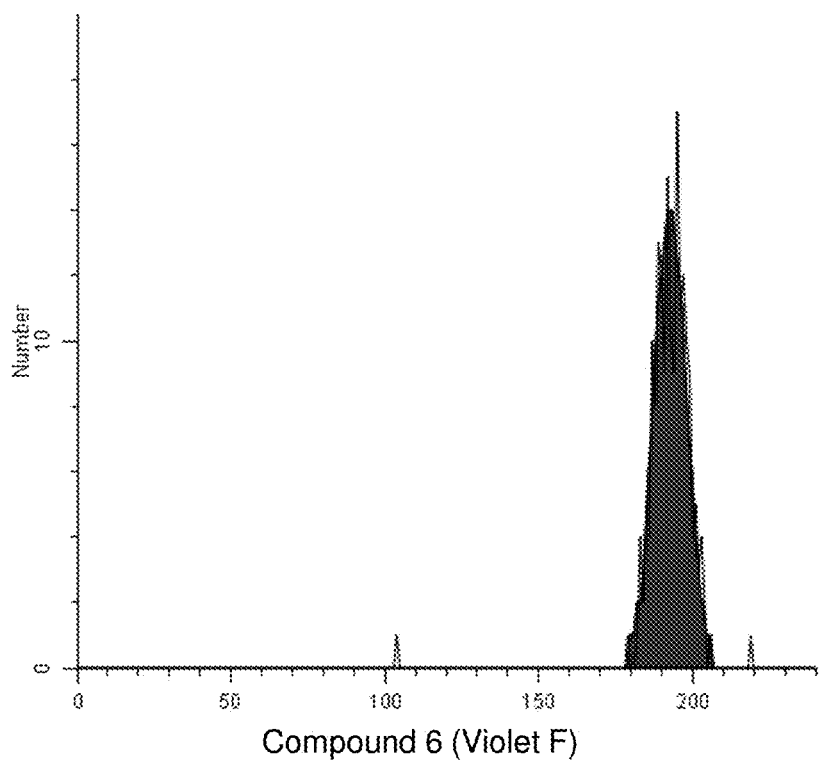
Figure 1K:
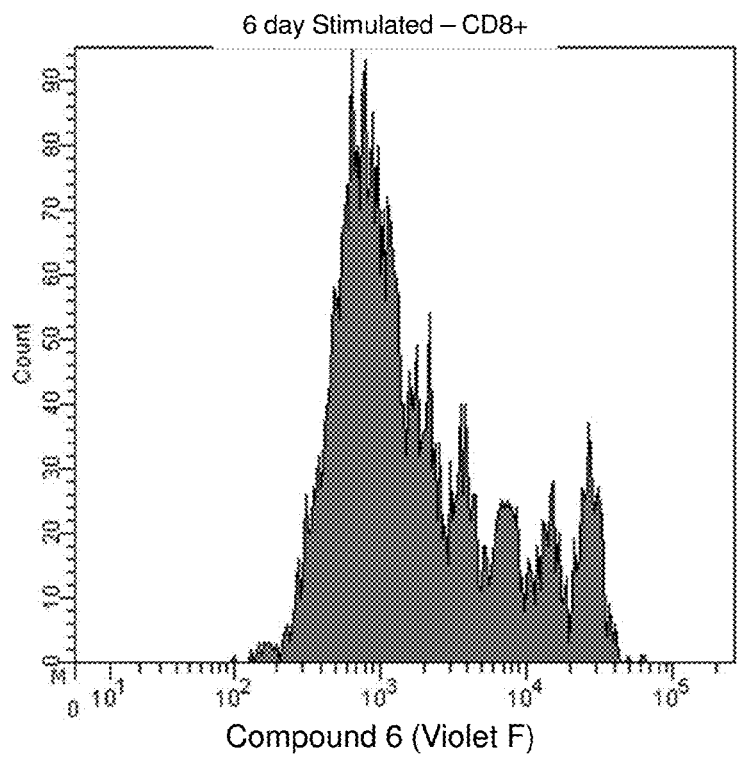
Figure 1L:
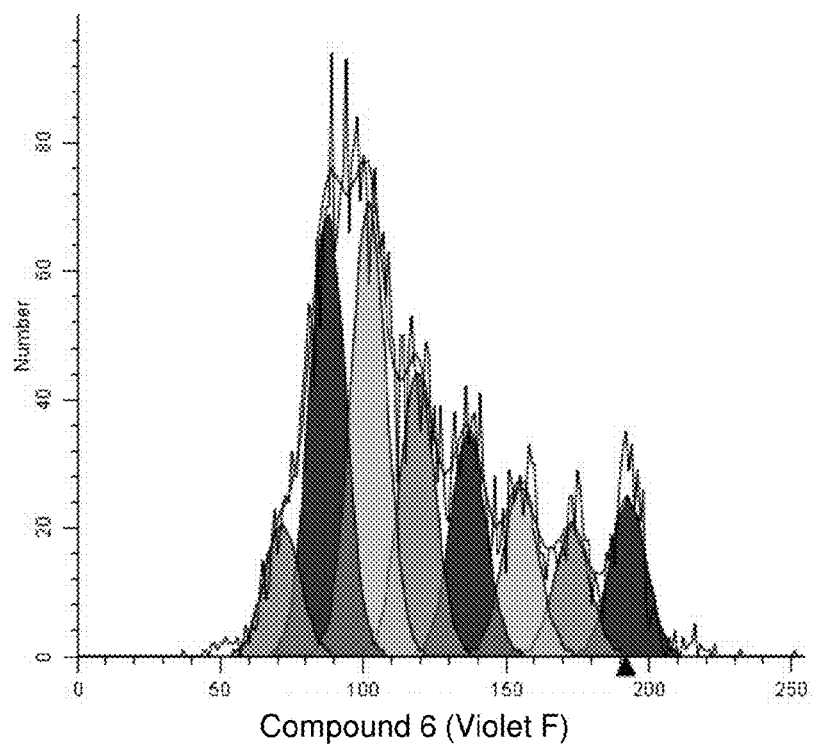
Figure 1M:
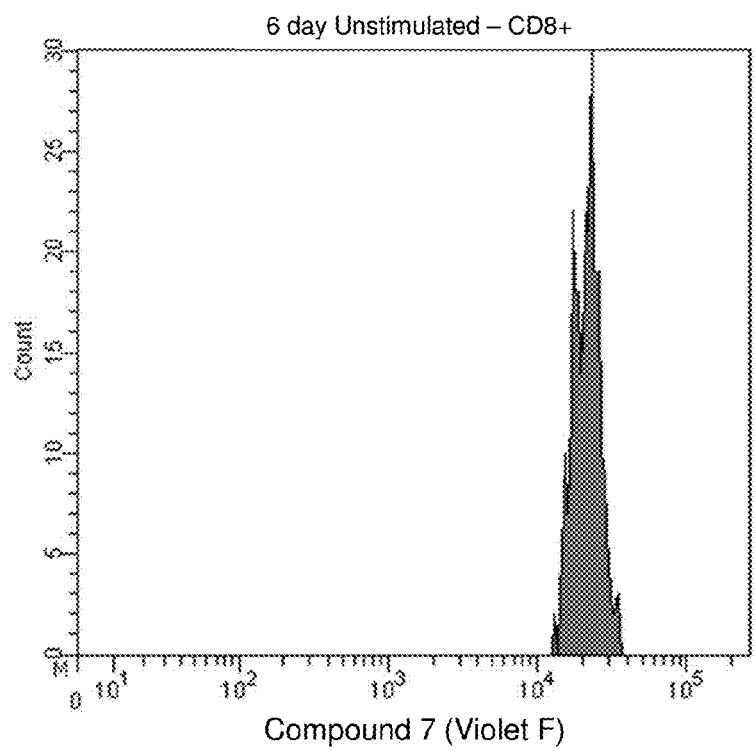
Figure 1N:
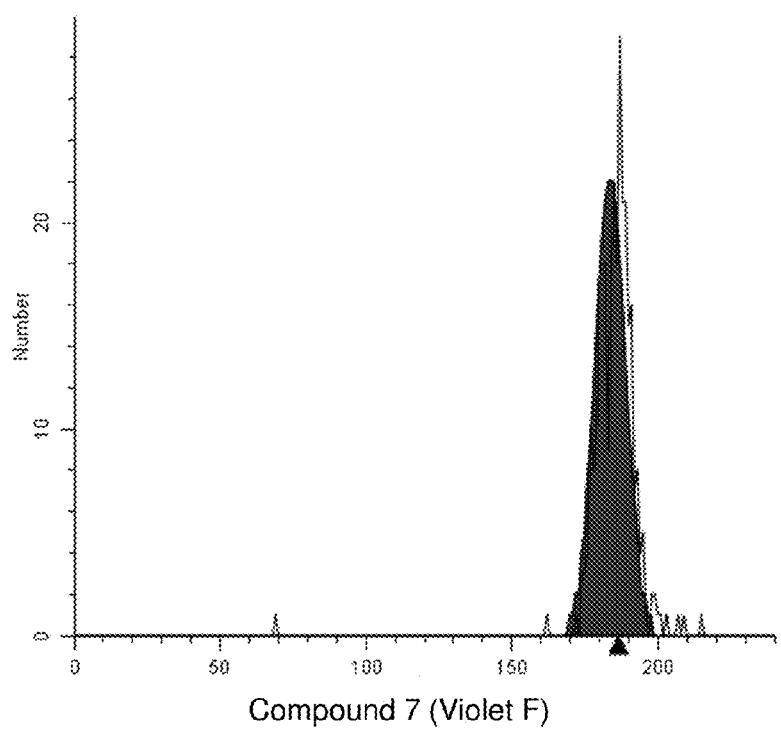
Figure 1O:
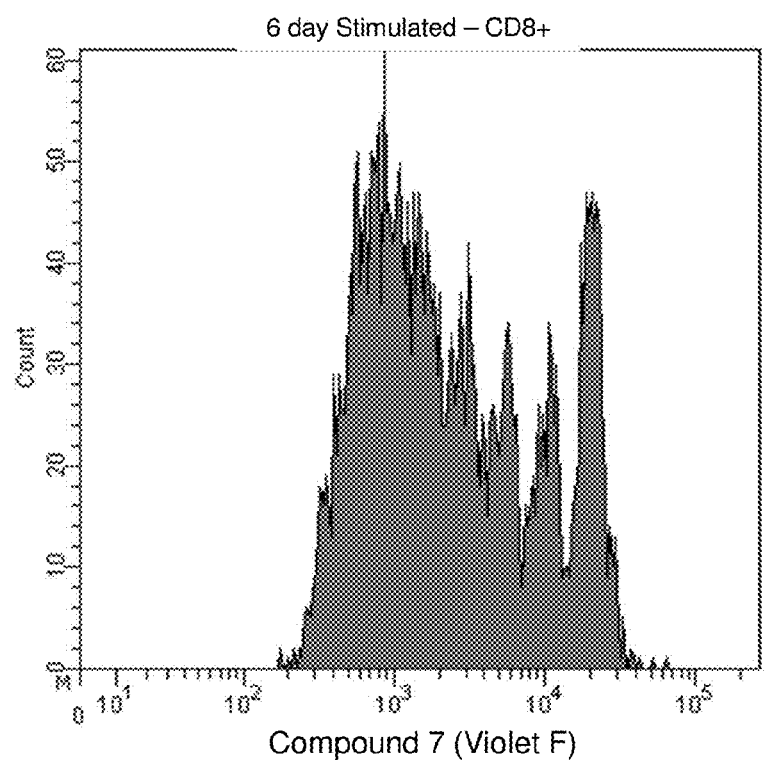

The present invention includes compounds, methods, and kits for long-term tracking of cell proliferation, differentiation, and/or function. The compounds of the present invention are novel cell-tracking reagents, efficiently excitable with a 405 nm violet laser, that provide bright fluorescence intensity, uniform cell staining, and good retention within cells as well as low toxicity toward cells. The cell-tracking reagents of the present invention are 7-hydroxycoumarin-based fluorophores, including chemically-reactive fluorophores and conjugates of such fluorophores. These cell-tracking reagents may be used in place of and/or in combination with other currently-available cell-tracking reagents, such as, for example, the 488 nm-excitable reagents CFDA-SE and/or Green Fluorescent Protein (GFP) as well as the 647 nm-excitable red-emitting dye PKH26, to track and/or stain otherwise indistinguishable cell populations in mixed cell cultures via flow cytometry and/or fluorescence microscopy, respectively. The present invention also includes processes for preparing and using the novel cell-tracking reagents described herein in the disclosed methods and kits of the present invention.

It is to be understood that this invention is not limited to specific compositions or process steps, as such may vary. It should also be noted that, as used in this specification and the appended claims, the singular form "a", "an" and "the" include plural references unless the context clearly dictates otherwise.

Unless defined otherwise, all technical and scientific terms used herein have the same meaning as commonly understood by one of ordinary skill in the art to which the present invention is related.

As used herein, "alkyl" refers to a hydrocarbon that is optionally linear or branched, and saturated. Similarly, the alkyl portions of perfluoroalkyl, alkoxy, alkylthio, monoalkylamino, dialkylamino or alkylamido groups are optionally linear or branched, and saturated.

As used herein, "aryl" refers to a phenyl moiety that is optionally and independently substituted by H, halogen, cyano, azido, sulfonic acid, alkali or ammonium salt of sulfonic acid, carboxylic acid, biologically compatible salt of carboxylic acid, nitro, alkyl, perfluoroalkyl, alkoxy, alkylthio, amino, monoalkylamino, dialkylamino or alkylamido.

As used herein, "heteroaryl" refers to a 5- or 6-membered aromatic heterocycle that is optionally fused to an additional six-membered aromatic ring or to one 5- or 6-membered heteroaromatic ring, said heteroaromatic ring containing 1-3 heteroatoms that are selected from the group consisting of O, N and S in any combination. Any heteroaryl substituent is attached by a single bond, and is optionally and independently substituted one or more times by H, halogen, alkyl having 1-6 carbons, or alkoxy having 1-6 carbons. Selected examples of heteroaryl substituents are pyrrole, thiophene, or furan (single ring, single hetero atom), oxazole, isoxazole, oxadiazole, or imidazole (single ring, multiple hetero atoms). Examples of multi-ring heteroaryl groups include benzoxazole, benzothiazole, benzimidazole (multi-ring, multiple hetero atoms), benzofuran or indole (multi-ring, single hetero atom).

As used herein, "a pharmaceutically acceptable salt" or "a biologically compatible salt" is a counterion that is not toxic as used, and does not have a substantially deleterious effect on biomolecules. Examples of such salts include, among others, $K^+$, $Na^+$, $Cs^+$, $Li^+$, $Ca^{++}$, $Mg^{++}$, $Cl^-$, $AcO^-$, and alkylammonium or alkoxyammonium salts.

As used herein, "alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

As used herein, "alkenyl" refers to alkenyl groups having from 2 to 6 carbon atoms, preferably 2 to 4 carbon atoms, and having at least 1 and preferably from 1 to 2 sites of alkenyl unsaturation. Such groups are exemplified, for example, by vinyl, allyl, and but-3-en-1-yl.

As used herein, "heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

As used herein, the term "Compound Violet" refers to a novel cell-tracking reagent (compound) of the present invention, which reagents are efficiently excitable with a 405 nm violet laser to provide bright fluorescence intensity for long-term monitoring of cell proliferation, differentiation, migration, location, and/or function.

As used herein, the term "dye" refers to a compound that emits light to produce an observable detectable signal.

As used herein, the term "fluorophore" or "fluorogenic" refers to a compound or a composition that demonstrates a change in fluorescence upon binding to a biological compound or analyte of interest and/or upon cleavage by an enzyme. The fluorophores of the present invention may be substituted to alter the solubility, spectral properties or physical properties of the fluorophore.

One illustrative aspect of the present invention provides a novel cell-tracking reagent (compound) having the structural formula (I):

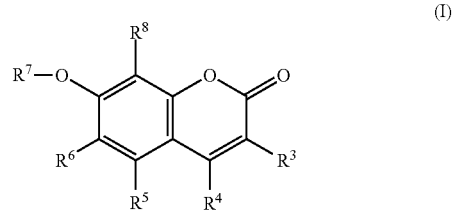

(I)

or a pharmaceutically acceptable salt thereof, wherein
$R^3$ is H, $C_1$-$C_{18}$ alkyl, $C_1$-$C_{18}$ perfluoroalkyl, CN, formyl, aryl, heteroaryl, arylcarbonyl, or —(C=O)—$NR^1R^2$ where $R^1$ and $R^2$ are independently H, $C_1$-$C_6$ alkyl, aryl, or $R^1$ and $R^2$ taken in combination are —$(CH_2)_2$-M-$(CH_2)_2$— where M is a single bond, —O—, —$CH_2$—, or —$NR^9$—, where $R^9$ is H or $C_1$-$C_6$ alkyl; or $R^3$ is -L-$R_X$ or -L-$S_C$;
$R^4$ is H, OH, CN, $C_1$-$C_{18}$ alkyl, $C_1$-$C_{18}$ perfluoroalkyl, sulfomethyl, biologically compatible salt of sulfomethyl, halomethyl, aryl, -L-$R_X$ or -L-$S_C$;
$R^5$ is H or $C_1$-$C_6$ alkoxy;
$R^6$ is Cl or F;
$R^7$ is H, or a monovalent moiety derived by removal of a hydroxy group from a phosphate, a thiophosphate, a sulfate, or a biologically compatible salt thereof; or a monovalent moiety derived by removal of a hydroxy group from a carboxy group of an aliphatic or aromatic carboxylic acid; or a monovalent moiety derived by removal of a hydroxy group from an alcohol or from a mono- or polysaccharide; or $R^7$ is a photolabile caging group; and
$R^8$ is H, Cl, F, $C_1$-$C_6$ alkoxy or $C_1$-$C_6$ alkyl;
wherein
aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamido; heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$-$C_6$ alkyl, or $C_1$-$C_6$ alkoxy; each L is independently a single covalent bond, or L is a covalent linkage having 1-24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds, nitrogen-sulfur bonds, sulfur-oxygen bonds, and carbon-sulfur bonds;

$R_X$ is a reactive group; and $S_C$ is a conjugated substance;

provided that at least one of $R^3$ and $R^4$ is -L-$R_X$ or -L-$S_C$; and that at least one of $R^6$ and $R^8$ is not F.

In one illustrative embodiment, at least one of $R^3$ and $R^4$ is -L-$R_X$, wherein $R_X$ is an acrylamide, a carboxylic acid, an activated ester of a carboxylic acid, an acyl azide, an acyl halide, hydroxy, an aldehyde, an alkyl halide, a sulfonate, an amine, an anhydride, an aniline, an aryl halide, an azide, an aziridine, a boronate, a carbodiimide, a diazoalkane, an epoxide, a glycol, a haloacetamide, a halotriazine, a hydrazine, a hydroxylamine, an imido ester, an isothiocyanate, a ketone, a maleimide, a sulfonyl halide, or a thiol group. In another illustrative embodiment, $R^3$ is -L-$R_X$ and $R_X$ is a succinimidyl ester. In another illustrative embodiment, $R^3$ is -L-$R_X$ and $R^4$ is H.

In another illustrative embodiment, $R^6$ is Cl. In another illustrative embodiment, at least one of $R^3$ and $R^4$ is -L-$S_C$ and $R^7$ is H. In another illustrative embodiment, at least one of $R^3$ and $R^4$ is -L-$S_C$, $R^7$ is H, and $S_C$ is an amino acid, a peptide, a protein, a monosaccharide, a polysaccharide, an ion-complexing moiety, a nucleotide, an oligonucleotide, a nucleic acid, a hapten, a drug, a toxin, a lipid, a phospholipid, a lipoprotein, a lipopolysaccharide, a liposome, a lipophilic polymer, a non-biological organic polymer, a polymeric microparticle, an animal cell, a plant cell, a bacterium, a yeast, or a virus. In another illustrative embodiment, $R^3$ is -L-$S_C$, $R^4$ is H, and $R^5$ is H. In another illustrative embodiment, $R^3$ is -L-$R_X$, $R^4$ is H, $R^5$ is H, and $R^7$ is a monovalent moiety derived by removal of a hydroxy group from an aliphatic carboxylic acid having 1-18 carbons, guanidinobenzoic acid, or sulfuric acid.

In another illustrative embodiment, $R^3$ or $R^4$ is -L-$R_X$ or -L-$S_C$ and $R^7$ is a monovalent moiety selected to enhance cellular permeability while being cleavable by an enzyme, e.g., intracellular esterases. In such embodiments, the monovalent moiety interferes with or alters the long-wavelength fluorescence properties of the cell-tracking reagent until the moiety is removed. In one such embodiment, $R^7$ is a monovalent moiety that is formally derived by removal of a hydroxy group from a carboxy group of an aliphatic or aromatic carboxylic acid. Preferably, $R^7$ is a monovalent moiety derived by removal of a hydroxy group from a carboxylic acid such as acetic acid, propionic acid, or butyric acid. Without being bound to theory, it is believed that cell-tracking reagents (IIa, IIb) of the present invention diffuse readily into cells, wherein intracellular cleavage of $R^7$ results in bright, long-wavelength fluorophores that upon concurrent or subsequent reaction with intracellular proteins (e.g.) via $R_X$ generate conjugates (IIIa, IIIb, $R^7$ is H) that would be expected to be retained inside the cells during the processes of cell division, maintenance and/or growth.

Selected embodiments of cell-tracking reagents (compounds IIa and IIb) of the present invention are listed below where $R^3$, $R^4$, $R^5$, $R^6$, $R^7$, $R^8$, L, and $R_X$ are as defined above (*$R^7$=Ac=Acetyl, *$R^7$=Acm=Acetoxymethyl).

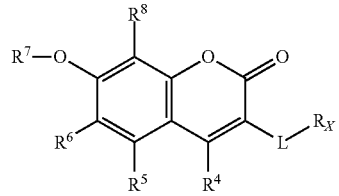

IIa

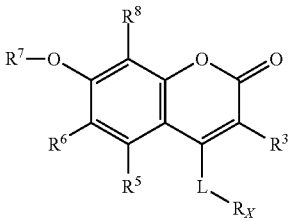

IIb

| Compound | $R^3$ | $R^4$ | $R^5$ | $R^6$ | *$R^7$ | $R^8$ |
|---|---|---|---|---|---|---|
| IIa$_1$ | L—CO$_2$Su | H | H | Cl | Ac | H |
| IIa$_2$ | L—CO$_2$Su | H | H | Cl | Acm | H |
| IIa$_3$ | L—CO$_2$Su | H | H | F | Ac | H |
| IIa$_4$ | L—CON$_3$ | H | H | Cl | Acm | Cl |
| IIa$_5$ | L—NH$_2$ | H | H | Cl | Ac | Cl |
| IIa$_6$ | L—N$_3$ | H | H | Cl | Acm | H |
| IIa$_7$ | L—NCO | H | H | Cl | Ac | H |
| IIa$_8$ | L—CHO | H | H | F | Ac | H |
| IIa$_9$ | L-Maleimide | H | H | F | Acm | H |
| IIa$_{10}$ | L—NHNH$_2$ | H | H | F | Ac | Cl |
| IIb$_1$ | H | L—CO$_2$Su | H | Cl | Ac | H |
| IIb$_2$ | H | L—CO$_2$Su | H | Cl | Acm | H |
| IIb$_3$ | H | L—CO$_2$Su | H | F | Ac | H |
| IIb$_4$ | H | L—CON$_3$ | H | Cl | Ac | Cl |
| IIb$_5$ | H | L—NH$_2$ | H | Cl | Acm | Cl |
| IIb$_6$ | H | L—N$_3$ | H | Cl | Ac | H |
| IIb$_7$ | H | L—NCO | H | Cl | Acm | H |
| IIb$_8$ | H | L—CHO | H | F | Ac | Cl |
| IIb$_9$ | H | L-Maleimide | H | F | Ac | H |
| IIb$_{10}$ | H | L—NHNH$_2$ | H | F | Acm | H |

Another illustrative aspect of the present invention provides a kit for tracking cell proliferation, differentiation, and/or function, the kit being compatible for use with, for example, flow cytometry and fluorescence microscopy, and including:

a) a novel cell-tracking reagent (compound) of structural formula (I):

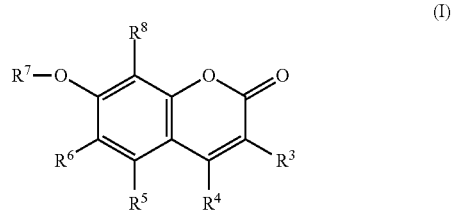

(I)

or a pharmaceutically acceptable salt thereof, wherein
$R^3$ is H, $C_1$-$C_{18}$ alkyl, $C_1$-$C_{18}$ perfluoroalkyl, CN, formyl, aryl, heteroaryl, arylcarbonyl, or —(C=O)—$NR^1R^2$ where $R^1$ and $R^2$ are independently H, $C_1$-$C_6$ alkyl, aryl, or $R^1$ and $R^2$ taken in combination are —($CH_2$)$_2$-M-($CH_2$)$_2$— where M is a single bond, —O—, —$CH_2$—, or —$NR^9$—, where $R^9$ is H or $C_1$-$C_6$ alkyl; or $R^3$ is -L-$R_X$;
$R^4$ is H, OH, CN, $C_1$-$C_{18}$ alkyl, $C_1$-$C_{18}$ perfluoroalkyl, sulfomethyl, biologically compatible salt of sulfomethyl, halomethyl, aryl, or -L-$R_X$;
$R^5$ is H or $C_1$-$C_6$ alkoxy;
$R^6$ is Cl or F;
$R^7$ is a monovalent moiety derived by removal of a hydroxy group from a carboxy group of an aliphatic or aromatic carboxylic acid; or a monovalent moiety derived by removal of a hydroxy group from an alcohol or from a mono- or polysaccharide; and
$R^8$ is H, Cl, F, $C_1$-$C_6$ alkoxy or $C_1$-$C_6$ alkyl;
wherein
aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamido;
heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$-$C_6$ alkyl, or $C_1$-$C_6$ alkoxy;
each L is independently a single covalent bond, or L is a covalent linkage having 1-24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds, nitrogen-sulfur bonds, sulfur-oxygen bonds, and carbon-sulfur bonds; and
$R_X$ is a reactive group;
provided that at least one of $R^3$ and $R^4$ is -L-$R_X$; and that at least one of $R^6$ and $R^8$ is not F;
  b) an organic solvent; and
  c) a desiccant.

In one illustrative embodiment of the kit, the compound therein is excitable with a 405-nm violet laser. In another illustrative embodiment, $R_X$ is an acrylamide, a carboxylic acid, an activated ester of a carboxylic acid, an acyl azide, an acyl halide, hydroxy, an aldehyde, an alkyl halide, a sulfonate, an amine, an anhydride, an aniline, an aryl halide, an azide, an aziridine, a boronate, a carbodiimide, a diazoalkane, an epoxide, a glycol, a haloacetamide, a halotriazine, a hydrazine, a hydroxylamine, an imido ester, an isothiocyanate, a ketone, a maleimide, a sulfonyl halide, or a thiol group. In another illustrative embodiment, $R_X$ is a carboxylic acid, an activated ester of a carboxylic acid, an amine, a maleimide, an iodoacetamide, an isothiocyanate, or a halomethyl.

In another illustrative embodiment of the kit, $R_X$ is a succinimidyl ester. In another illustrative embodiment, $R^3$ is -L-$R_X$ and $R^6$ is Cl. In another illustrative embodiment, $R^7$ is a monovalent moiety derived by removal of a hydroxy group from an aliphatic carboxylic acid having 1-18 carbons. In another illustrative embodiment, $R^7$ is a monovalent moiety derived by removal of a hydroxy group from acetic acid, propionic acid, or butyric acid. In another illustrative embodiment, the organic solvent is DMSO.

Another illustrative aspect of the present invention provides a method for tracking cell proliferation, differentiation, and/or function, the method being compatible for use with, for example, flow cytometry and fluorescence microscopy, and including:
  a) incubating a mixture of cells and a novel cell-tracking reagent (compound) of structural formula (I):

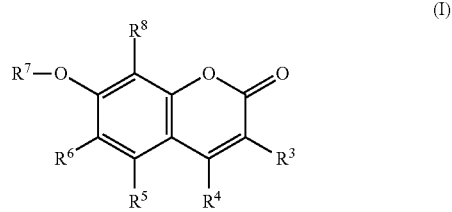

or a pharmaceutically acceptable salt thereof, wherein
$R^3$ is H, $C_1$-$C_{18}$ alkyl, $C_1$-$C_{18}$ perfluoroalkyl, CN, formyl, aryl, heteroaryl, arylcarbonyl, or —(C=O)—$NR^1R^2$ where $R^1$ and $R^2$ are independently H, $C_1$-$C_6$ alkyl, aryl, or $R^1$ and $R^2$ taken in combination are —($CH_2$)$_2$-M-($CH_2$)$_2$— where M is a single bond, —O—, —$CH_2$—, or —$NR^9$—, where $R^9$ is H or $C_1$-$C_6$ alkyl; or $R^3$ is -L-$R_X$;
$R^4$ is H, OH, CN, $C_1$-$C_{18}$ alkyl, $C_1$-$C_{18}$ perfluoroalkyl, sulfomethyl, biologically compatible salt of sulfomethyl, halomethyl, aryl, or -L-$R_X$;
$R^5$ is H or $C_1$-$C_6$ alkoxy;
$R^6$ is Cl or F;
$R^7$ is a monovalent moiety derived by removal of a hydroxy group from a carboxy group of an aliphatic or aromatic carboxylic acid; or a monovalent moiety derived by removal of a hydroxy group from an alcohol or from a mono- or polysaccharide; and
$R^8$ is H, Cl, F, $C_1$-$C_6$ alkoxy or $C_1$-$C_6$ alkyl;
wherein
aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamido;
heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$-$C_6$ alkyl, or $C_1$-$C_6$ alkoxy;
each L is independently a single covalent bond, or L is a covalent linkage having 1-24 nonhydrogen atoms selected from the group consisting of C, N, O and S and is composed of any combination of single, double, triple or aromatic carbon-carbon bonds, carbon-nitrogen bonds, nitrogen-nitrogen bonds, carbon-oxygen bonds, nitrogen-sulfur bonds, sulfur-oxygen bonds, and carbon-sulfur bonds; and
$R_X$ is a reactive group;
provided that at least one of $R^3$ and $R^4$ is -L-$R_X$; and that at least one of $R^6$ and $R^8$ is not F;
  b) providing a stimulus to the mixture to elicit a fluorescent signal; and
  c) analyzing the stimulated mixture.

In one illustrative embodiment of the method, the compound therein is excitable with a 405-nm violet laser. In another illustrative embodiment, the method includes a second compound excitable at 488 nm or 647 nm. In another illustrative embodiment, the method includes a second compound where the second compound is CFDA-SE or GFP. In another illustrative embodiment, the method includes a second compound where the second compound is PKH26.

In another illustrative embodiment of the method, $R_X$ is an acrylamide, a carboxylic acid, an activated ester of a carboxylic acid, an acyl azide, an acyl halide, hydroxy, an aldehyde, an alkyl halide, a sulfonate, an amine, an anhydride, an aniline, an aryl halide, an azide, an aziridine, a boronate, a carbodiimide, a diazoalkane, an epoxide, a glycol, a haloacetamide, a halotriazine, a hydrazine, a hydroxylamine, an imido ester, an isothiocyanate, a ketone, a maleimide, a sulfonyl halide, or a thiol group. In another illustrative embodiment, $R_X$ is a carboxylic acid, an activated ester of a carboxylic acid, an amine, a maleimide, an iodoacetamide, an isothiocyanate, or a halomethyl. In another illustrative embodiment, $R_X$ is a succinimidyl ester.

In another illustrative embodiment of the method, $R^7$ is a monovalent moiety derived by removal of a hydroxy group from an aliphatic carboxylic acid having 1-18 carbons. In another illustrative embodiment, $R^7$ is a monovalent moiety derived by removal of a hydroxy group from acetic acid, propionic acid, or butyric acid. In another illustrative embodiment, step a) is conducted for approximately 20 minutes. In another illustrative embodiment, step b) and step c) are carried out concurrently. In another illustrative embodiment, step b) and step c) involve flow cytometry.

Another illustrative aspect of the present invention provides a process for preparing a novel cell-tracking reagent (compound) of structural formula IIIa or IIIb

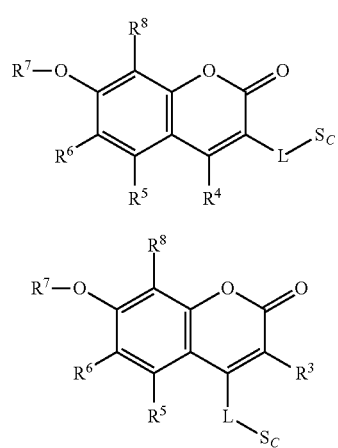

the process comprising:
a) reacting a novel cell-tracking reagent (compound) of structural formula IIa or IIb, respectively

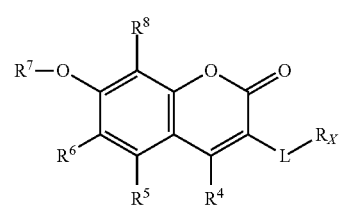

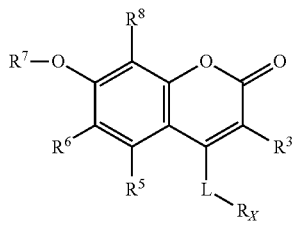

with a substance S to be conjugated thereto, thereby resulting in a conjugated substance $S_C$, wherein $R^3$, $R^4$, $R^5$, $R^6$, $R^7$, $R^8$, L, $R_X$, and $S_C$ are as defined herein.

The cell-tracking reagents (compounds) of the present invention containing a reactive group $R_X$ (i.e., IIa, IIb) fluorescently label a wide variety of organic substances that contain functional groups with suitable reactivity, resulting in chemical attachment, i.e., conjugation, of the substance (thereby affording a conjugated substance, $S_C$) and formation of cell-tracking reagents that are themselves conjugates (i.e., IIIa, IIIb). Most preferably, but not exclusively, the conjugated substance of the present invention is an intracellular amino acid, peptide, protein, nucleotide, oligonucleotide, nucleic acid, lipid, phospholipid, lipoprotein, or lipopolysaccharide. The reactive group and functional group are typically an electrophile and a nucleophile, respectively, that can generate a covalent linkage. Alternatively, the reactive group is a photoactivatable group that becomes chemically reactive only after illumination with light of an appropriate wavelength. Selected examples of functional groups and linkages, where the reaction of an electrophilic group and a nucleophilic group yields a covalent linkage, as well as a general discussion of dye-conjugate chemistry, are provided in U.S. Pat. No. 5,830,912 the disclosure of which is incorporated herein by reference in its entirety.

The process of preparing dye conjugates using reactive dyes, which process is amenable to preparing cell-tracking reagents (compounds) of the present invention containing a conjugated substance ($S_C$) using cell-tracking reagents (compounds) of the present invention containing a reactive group ($R_X$), is well documented, e.g., by Hermanson (see, Hermanson G T, *Bioconjugate Techniques* (Academic Press 1996)), Haugland (see, Haugland R P, MOLECULAR PROBES HANDBOOK OF FLUORESCENT PROBES AND RESEARCH CHEMICALS, Sets 1-7 (1992)), Brinkley et al. (see, Brinkley et al., *Bioconjugate Chem.*, 3, 2 (1992)), and Haugland et al. (see, Haugland et al., *Meth. Mol. Biol.* 45, 205 (1995)), the disclosures of which are hereby incorporated herein by reference in their entirety. Nonetheless, the cell-tracking reagents (compounds) of the present invention containing a conjugated substance ($S_C$), i.e., reagents (compounds) of general formulae IIIa and IIIb, typically result from adding a cell-tracking reagent (compound) of the present invention containing a reactive group ($R_X$), i.e., a reagent (compound) of general formulae IIa and IIb, to a preparation of cells as described in Biological Application Examples 1-5 herein.

Another illustrative aspect of the present invention provides a process for preparing a novel cell-tracking reagent (compound) of structural formula IIa or IIb

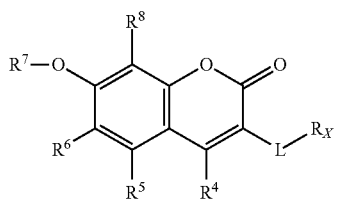

(IIa)

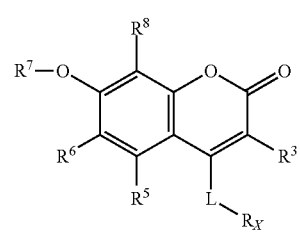

(IIb)

for use in the disclosed methods and kits of the present invention, wherein $R^3$, $R^4$, $R^5$, $R^6$, $R^7$, $R^8$, L, and $R_X$ are as defined herein.

In one illustrative embodiment, a novel cell-tracking reagent (compound) of structural formula IIa, wherein L is a single covalent bond, is prepared as shown in Scheme I.

Scheme I

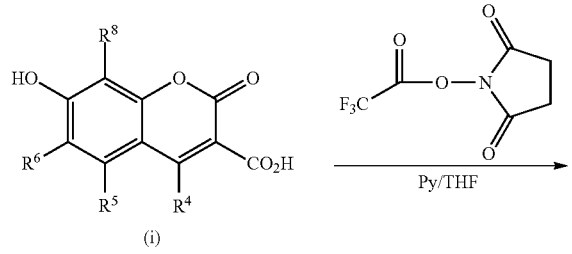

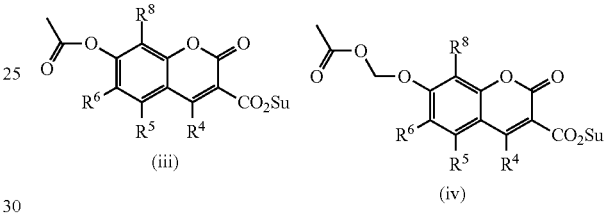

Esterification of hydroxycoumarin carboxylic acid (i) with succinimidyl trifluoroacetate in pyridine/THF affords hydroxycoumarin succinimidyl ester (ii), which upon reaction with acetyl chloride or bromomethyl acetate in N,N-dimethylacetamide (N,N-DMA) in the presence of diisopropylethylamine (DIEA) affords cell-tracking reagent (iii) and cell-tracking reagent (iv), respectively. It is anticipated that the same series of chemical reactions will afford the corresponding novel cell-tracking reagents (compounds) of structural formula IIb.

In another illustrative embodiment, a novel cell-tracking reagent (compound) of structural formula IIa, wherein L is based on isonipecotic acid, is prepared as shown in Scheme II.

Scheme II

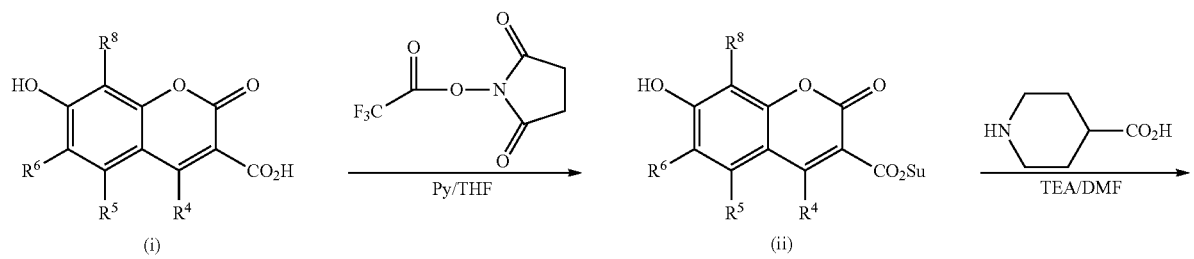

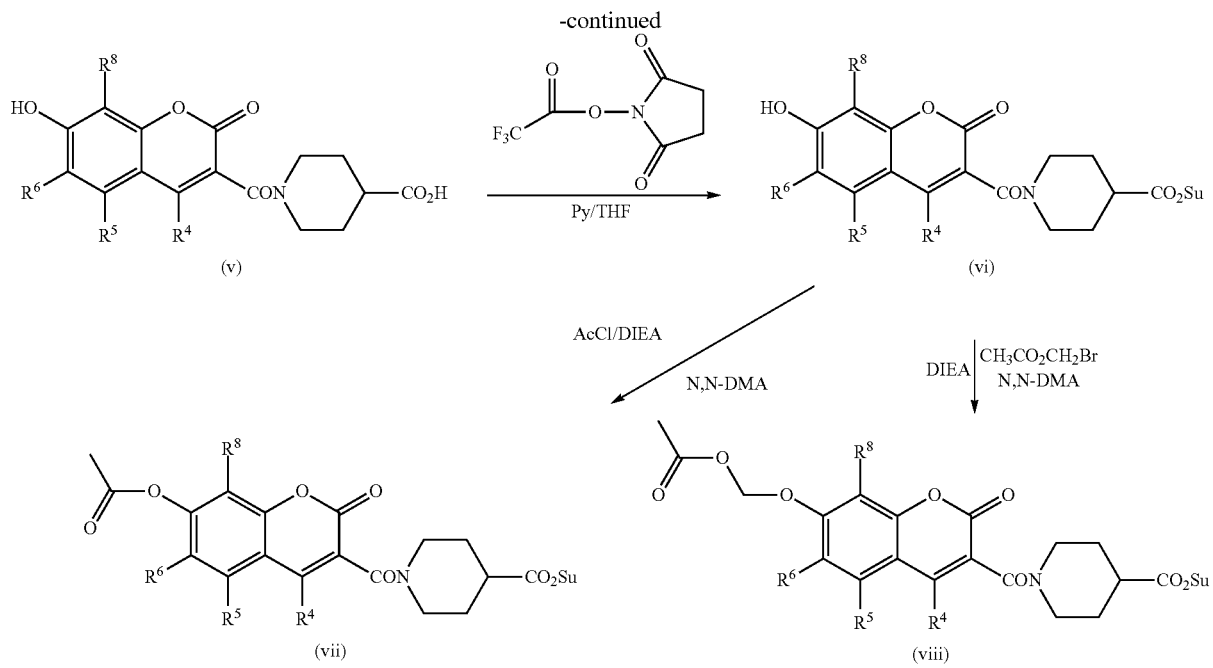

Esterification of hydroxycoumarin carboxylic acid (i) with succinimidyl trifluoroacetate in pyridine/THF affords hydroxycoumarin succinimidyl ester (ii), which upon reaction with isonipecotic acid in dimethylformamide (DMF) in the presence of triethylamine (TEA) yields hydroxycoumarin carboxylic acid (v). Esterification of hydroxycoumarin carboxylic acid (v) with succinimidyl trifluoroacetate in pyridine/THF affords hydroxycoumarin succinimidyl ester (vi), which upon reaction with acetyl chloride or bromomethylacetate in N,N-dimethylacetamide (N,N-DMA) in the presence of diisopropylethylamine (DIEA) affords cell-tracking reagent (vii) and cell-tracking reagent (viii), respectively. It is anticipated that the same series of chemical reactions will afford the corresponding novel cell-tracking reagents (compounds) of structural formula IIb.

In another illustrative embodiment, a novel cell-tracking reagent (compound) of structural formula IIa, wherein L is based on 6-aminocaproic acid, is prepared as shown in Scheme II wherein 6-aminocaproic acid is used in place of isonipecotic acid to ultimately afford cell-tracking reagent (ix) and cell-tracking reagent (x). It is anticipated that the same series of chemical reactions will afford the corresponding novel cell-tracking reagents (compounds) of structural formula IIb.

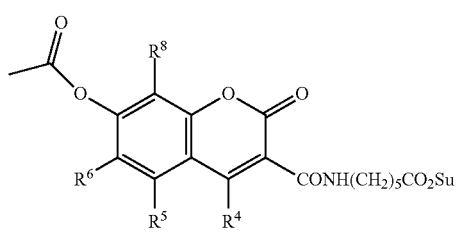

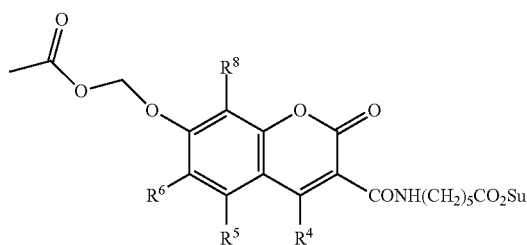

A detailed description of the present invention having been provided above, the following examples are given for the purpose of illustrating the invention and shall not be construed as being a limitation on the scope of the invention or claims.

EXAMPLES

Chemical Synthesis of Cell-Tracking Reagents (Compounds)

Preparation of Cell-Tracking Reagents of the Present Invention: Compounds (2) and (3)

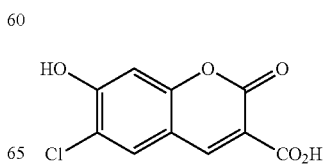 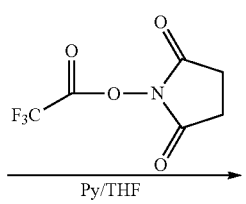

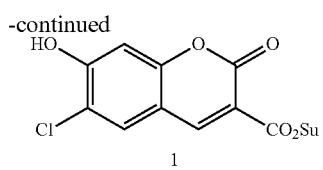

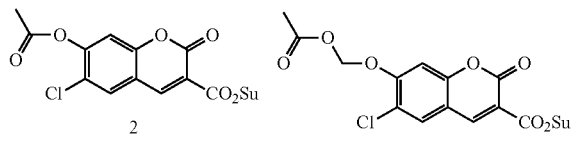

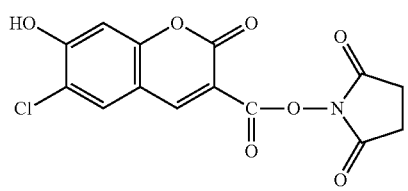

To 3-carboxy-6-chloro-7-hydroxycoumarin (400 mg, 1.66 mmol) in anhydrous THF (20 mL) was added anhydrous pyridine (0.60 mL, 7.47 mmol) and then succinimidyl trifluoroacetate (1.23 g, 5.81 mmol). The resulting solution was stirred at RT overnight. DMF (30 mL) was then added to the reaction mixture. The solution was diluted with EtOAc (100 mL), and then poured into 1N HCl (150 mL). Following extraction with EtOAc, the resulting organic phase was dried over anhydrous Na$_2$SO$_4$, filtered to remove Na$_2$SO$_4$, and the resulting filtrate evaporated on a rotary evaporator under reduced pressure to give Compound 1 (540 mg, 96%) as a yellowish solid.

TLC: R$_f$=0.39 (silica gel, 20:1:0.5 CHCl$_3$/MeOH/AcOH). $^1$H NMR (400 MHz, DMSO-d$_6$): δ(ppm) 12.10 (br. s, 1H, ArOH), 8.99 (s, 1H, ArH), 8.14 (s, 1H, ArH), 6.93 (s, 1H, ArH), 2.90 (s, 4H, CH$_2$CH$_2$). UV-Vis (free acid, pH 7.4 buffer): λmax=389 nm. Emission (free acid, pH 7.4 buffer): λmax=442 nm.

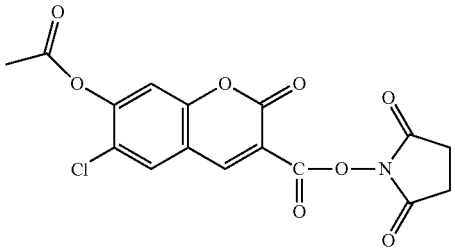

To Compound 1 (34 mg, 0.10 mmol) in anhydrous N,N-dimethylacetamide (5 mL) was added N,N-diisopropylethylamine (0.092 mL, 0.525 mmol) and then acetyl chloride (0.071 mL, 1.05 mmol). The resulting solution was stirred for 10 min at RT, then diluted with EtOAc (50 mL), and poured into 1N HCl (50 mL). Following extraction with EtOAc, the resulting organic phase was dried over anhydrous Na$_2$SO$_4$, filtered to remove Na$_2$SO$_4$, and the resulting filtrate evaporated on a rotary evaporator under reduced pressure to give Compound 2 (35 mg, 92%) as an off-white solid.

TLC: R$_f$=0.70 (silica gel, 25:1 CHCl$_3$/MeOH). $^1$H NMR (400 MHz, DMSO-d$_6$): δ(ppm) 9.08 (s, 1H, ArH), 8.34 (s, 1H, ArH), 7.65 (s, 1H, ArH), 2.91 (s, 4H, CH$_2$CH$_2$), 2.40 (s, 3H, CH$_3$).

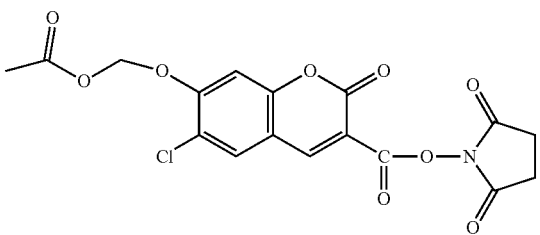

Compound 3 can be prepared from 3-carboxy-6-chloro-7-hydroxycoumarin, succinimidyl ester (Compound 1) and bromomethyl acetate by following the same general procedure for the transformation of Compound 1 to Compound 2.

Preparation of Cell-Tracking Reagents of the Present Invention: Compounds (6) and (7)

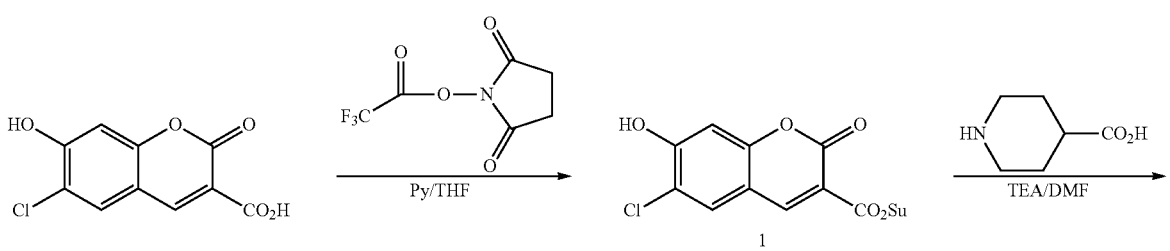

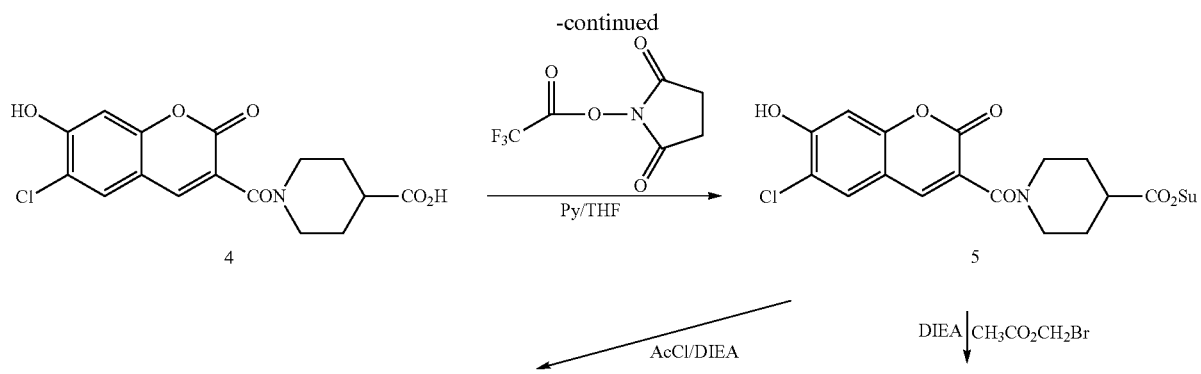

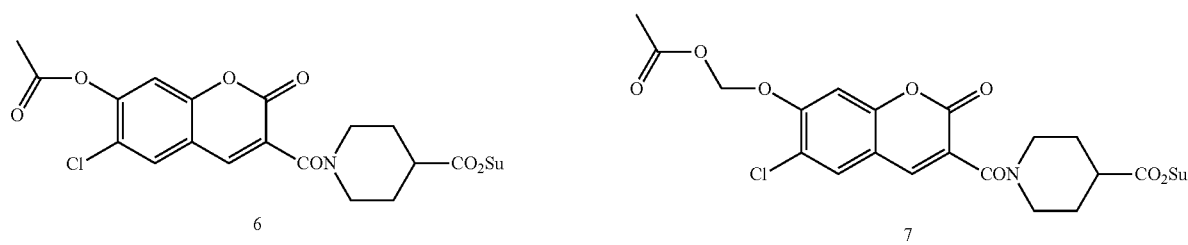

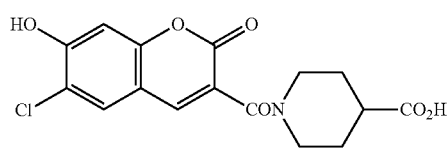

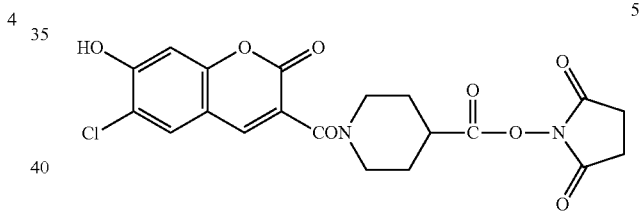

To isonipecotic acid (860 mg, 6.66 mmol) and triethylamine (4 mL) in DMF (20 mL) water was added slowly until the suspension dissolved. The resulting solution was stirred at RT for 1 h and then added to Compound 1 (550 mg, 1.63 mmol) in DMF (20 mL) cooled in an ice/water bath. The mixture became cloudy at which point water was added slowly until the suspension dissolved. Stirring of the mixture was continued at ice/water bath temperature for 3 h and then at RT overnight.

The reaction mixture was diluted with EtOAc (100 mL) and then poured into 1N HCl (100 mL). Following extraction with EtOAc, the resulting organic phase was dried over anhydrous $Na_2SO_4$, filtered to remove $Na_2SO_4$, and the resulting filtrate evaporated on a rotary evaporator under reduced pressure. The resulting residue was purified on a silica gel column with $CHCl_3$, EtOAc and acetic acid to give Compound 4 (537 mg, 94%) as an off-white solid.

TLC: $R_f$=0.22 (silica gel, 20:1:0.5 $CHCl_3$/MeOH/AcOH). $^1$H NMR (400 MHz, $CD_3OD$): δ(ppm) 7.97 (s, 1H, ArH), 7.72 (s, 1H, ArH), 6.90 (s, 1H, ArH), 4.40 (m, 1H, CH), 3.71 (m, 1H, CH), 3.33 (m, 1H, CH), 3.27 (m, 1H, CH), 2.65 (m, 1H, CH), 2.06 (m, 1H, CH), 1.97 (m, 1H, CH), 1.74 (m, 2H, 2×CH). MS(ESI$^-$)[m/z]: 352 [M+H]$^-$. UV-Vis (pH 9 buffer): λmax=390 nm. Emission (pH 9 buffer): λmax=450 nm.

Compound 5 was prepared from Compound 4 (230 mg, 0.65 mmol) by following the same general procedure for the preparation of Compound 1. Compound 5 (277 mg, 95%) was obtained as a yellowish solid.

TLC: $R_f$=0.41 (silica gel, 20:1:0.5 $CHCl_3$/MeOH/AcOH). $^1$H NMR (400 MHz, DMSO-$d_6$): δ(ppm) 11.60 (s, 1H, ArOH), 8.16 (s, 1H, ArH), 8.05 (s, 1H, ArH), 6.94 (s, 1H, ArH), 4.30 (m, 1H, CH), 3.67 (m, 1H, CH), 3.18 (m, 2H, 2×CH), 3.07 (m, 1H, CH), 2.82 (s, 4H, $CH_2CH_2$), 2.03 (m, 1H, CH), 1.92 (m, 1H, CH), 1.65 (m, 2H, 2×CH).

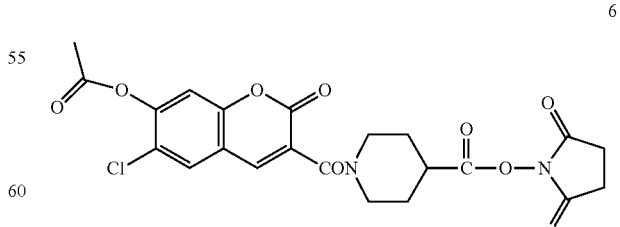

Compound 6 was prepared from Compound 5 (47 mg, 0.105 mmol) by following the same general procedure for the preparation of Compound 2. Compound 6 (25 mg, 49%) was obtained as an off-white solid.

TLC: $R_f$=0.48 (silica gel, 25:1 CHCl$_3$/MeOH). $^1$H NMR (400 MHz, CDCl$_3$): δ (ppm) 7.85 (s, 1H, ArH), 7.65 (s, 1H, ArH), 7.23 (s, 1H, ArH), 4.34 (m, 1H, CH), 3.60 (m, 1H, CH), 3.30 (m, 2H, 2×CH), 3.02 (m, 1H, CH), 2.87 (s, 4H, CH$_2$CH$_2$), 2.42 (s, 3H, CH$_3$), 2.05 (m, 2H, 2×CH), 2.00 (m, 2H, 2×CH).

ArH), 7.16 (s, 1H, ArH), 5.89 (s, 2H, OCH$_2$O), 4.35 (m, 1H, CH), 3.62 (m, 1H, CH), 3.33 (m, 2H, 2×CH), 3.04 (m, 1H, CH), 2.87 (s, 4H, CH$_2$CH$_2$), 2.18 (s, 3H, CH$_3$), 2.13 (m, 2H, 2×CH), 2.01 (m, 2H, 2×CH).

Preparation of Cell-Tracking Reagents (10) and (11)

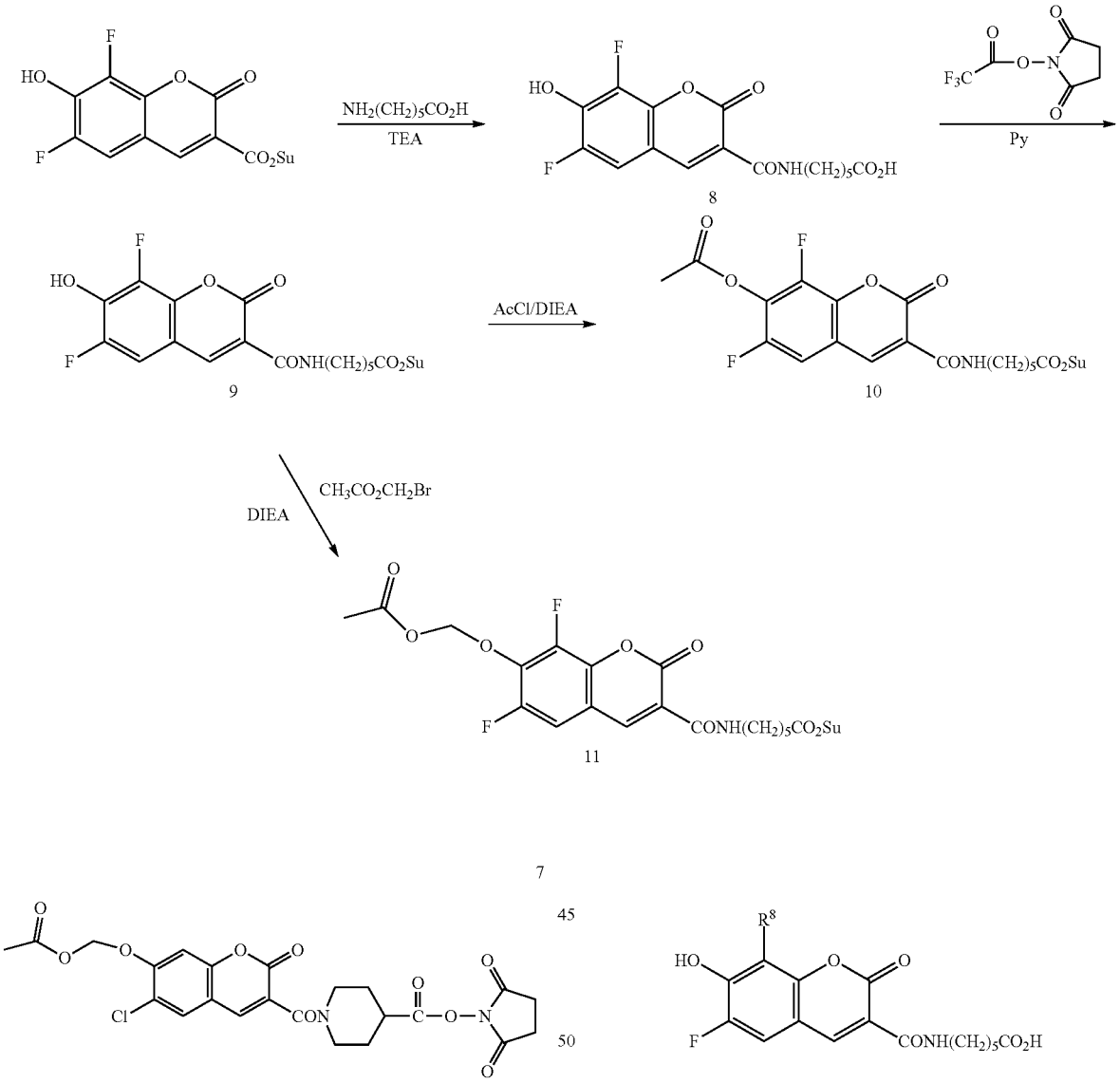

To Compound 5 (280 mg, 0.62 mmol) in anhydrous N,N-dimethylacetamide (15 mL) was added N,N-diisopropylethylamine (0.38 mL, 2.17 mmol) and then bromomethyl acetate (0.36 mL, 3.72 mmol). The resulting solution was stirred for 6 h at RT, then diluted with EtOAc (100 mL), and poured into 1N HCl (100 mL). Following extraction with EtOAc, the resulting organic phase was dried over anhydrous Na$_2$SO$_4$, filtered to remove Na$_2$SO$_4$, and the resulting filtrate evaporated on a rotary evaporator under reduced pressure. The resulting residue was purified on a silica gel column with CHCl$_3$ and EtOAc to give Compound 7 (191 mg, 59%) as an off-white solid.

TLC: $R_f$=0.50 (silica gel, 25:1 CHCl$_3$/MeOH). $^1$H NMR (400 MHz, CDCl$_3$): δ (ppm) 7.84 (s, 1H, ArH), 7.57 (s, 1H, Compound 8 was prepared from 3-carboxy-6,8-difluoro-7-hydroxycoumarin, succinimidyl ester (40 mg, 0.12 mmol, prepared as described in U.S. Pat. No. 5,830,912) and 6-aminocaproic acid (70 mg, 0.53 mmol) by following the same general procedure for the transformation of Compound 1 to Compound 4. Compound 8 (50 mg, 94%) was obtained as a yellowish solid.

TLC: $R_f$=0.33 (silica gel, 20:1:0.5 CHCl$_3$/MeOH/AcOH). MS(ESI)[m/z]: 356 [M+H]$^-$. UV-Vis (pH 7.4 buffer): λmax=401 nm. Emission (pH 7.4 buffer): λmax=450 nm.

9

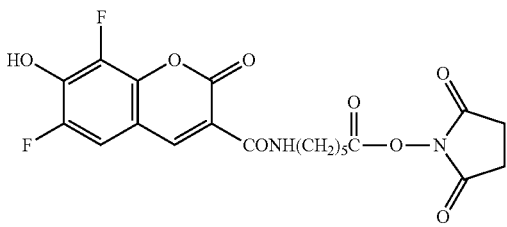

Compound 9 was prepared from Compound 8 (50 mg, 0.11 mmol) by following the same general procedure for the preparation of Compound 1. Compound 9 (46 mg, 92%) was obtained as a yellowish solid.

10

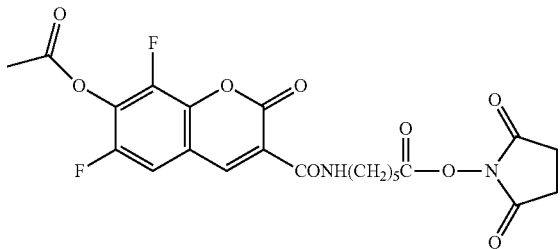

Compound 10 was prepared from Compound 9 by following the same procedures for the preparation of Compound 2.

11

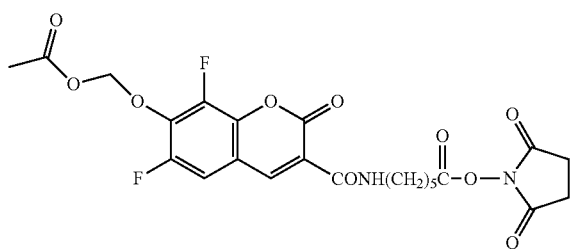

Compound 11 was prepared from Compound 9 (46 mg, 0.11 mmol) by following the same general procedure for the preparation of Compound 7. Compound 11 (50 mg, 89%) was obtained as an off-white solid.

TLC: $R_f$=0.52 (silica gel, 25:1 CHCl$_3$/MeOH). $^1$H NMR (400 MHz, DMSO-d$_6$): δ(ppm) 8.80 (s, 1H, ArH), 8.61 (t, 1H, CONH), 7.90 (m, 1H, ArH), 5.79 (s, 2H, OCH$_2$O), 3.31 (m, 2H, CH$_2$), 2.80 (s, 4H, CH$_2$CH$_2$), 2.68 (t, 2H, CH$_2$), 2.10 (s, 3H, CH$_3$), 1.69 (m, 2H, CH$_2$), 1.57 (m, 2H, CH$_2$), 1.41 (m, 2H, CH$_2$).

Biological Application Examples of Cell-Tracking Reagents (Compounds)

Example 1

Experimental Protocol:
Preparation of Culture Media

To 1 L of OpTimizer T-Cell Expansion Medium were added the following: 26 mL of T cell expansion supplement, 10 mL of 200 mM L-glutamine solution (final concentration=2 mM), and 1 ml of 50 mg/mL Gentamycin solution (final concentration=50 µg/mL). Complete media is stable for ~4 weeks when stored at 2-8° C. in the dark.

Preparation of HIl-2 Stock Solution

Acetic acid, 100 mM, was prepared by diluting 5 µL glacial (17M) acetic acid into 800 µL of dH$_2$O. Il-2, 40 µg, was dissolved in 400 µL of 100 mM acetic acid to make a 0.1 mg/mL solution; 20 µL aliquots of this solution were placed into microfuge tubes and stored at −20° C. One µL of this solution contains 100 ng of il-2.

CD3 Concentration

A 0.5 mL bottle of Caltag MHCD 0300 contains 100 µg of CD3; a 1 µL aliquot of this stock solution contains 200 ng of CD3.

Ficoll Separation of Mononuclear Cells from Whole Blood

Human peripheral blood mononuclear cells were isolated from whole blood using a Ficoll density gradient, then washed and resuspended in phosphate buffered saline (DPBS) at a concentration of 10$^6$/mL. The general procedure used is as follows:

1. Dilute 8 mL of whole blood into 8 mL of 1×PBS and mix well.
2. Add 6 mL Ficoll-Paque Plus to a 15-mL centrifuge tube, then layer 8 mL diluted whole blood on top.
3. Centrifuge 30 min at 400 g, then carefully remove the lymphocyte layer.
4. Resuspend cells in 25 mL DPBS buffer in a 50-mL conical tube.
5. Spin tube for 5 min at 200 g, pour off supernatant and resuspend in 25 mL DPBS.
6. Repeat wash step and resuspend in 300 µL of Isolation Buffer.
7. Count cells on cellometer; adjust cell concentration to 10$^6$ cells/mL Cell Staining Compound 2, Compound 6, Compound 7, and Carboxyfluorescein Diacetate Succinimidyl ester (CFSE) were each dissolved in anhydrous dimethylsulfoxide to a concentration of 1 mM. Aliquots, 4-mL, of cells were then stained with 4 µL of Compound 2, Compound 6, Compound 7, or CFSE for final staining concentrations of 1 µM. Cells were incubated with agitation at room temperature for 20 minutes. Then 2 mL of heat-inactivated Fetal Bovine Serum (FBS) were added, followed by 5 more minutes of incubation. Cells were washed twice with DPBS+10% FBS and resuspended in 4 mL of OpTmizer T-Cell Expansion Buffer (GIBCO) containing 2 mM L-glutamine, and 100,000 units penicillin and 100 mg streptomycin per liter. Aliquots (1-mL) of cells stained with Compound 2, Compound 6, Compound 7, or CFSE, and a 1-ml aliquot of unstained cells were then dispensed into a 24-well polystyrene plate and incubated at 37° C. and 5% CO$_2$ for 24 hours. One of the following four stimulus conditions were then applied individually to the cells: i) 200 ng anti-CD3 (2 µL), incubated on ice for 30 min, then transferred to culture plate and add 100 ng iL-2 per mL of culture media, ii) 5 µg/mL Concanavalin A (5 µL of a 1 mg/mL solution), iii) 75 µL CD3/CD28 T cell expander beads, or iv) no stimulus. The cells were then incubated for 72 additional hours at 37° C. and 5% CO$_2$. Aliquots (500-µL) of cells from each treatment were analyzed immediately following staining, and at 24 hours and six days after staining.

Sample Analysis:

Aliquots (500 µL) of cells were washed and resuspended in PBS, stained with mouse anti-human CD3 or CD8 R-phycoerythrin primary antibody conjugates for 15 minutes, then washed and stained with SYTOX® Red Dead Cell Stain for 5 minutes. Cells were then run through the Becton Dickinson (BD) LSRII Flow Cytometer. Fluorescence was collected using three lasers: the 405 nm excitation laser with 450/50 bandpass emission filter, the 488 nm excitation laser with 585/42 bandpass emission filter, and the 633 nm excitation laser with 660/20 bandpass emission filter. A gating strategy was employed to limit analysis to only the cells of interest. Cells were gated first on SYTOX® Red Dead Cell Stain negative (live) cells, then on R-phycoerythrin positive cells (CD3+ or CD8+ positive). These cells were then displayed on a fluorescence histogram with 405 nm excitation and 450/50 nm emission. CountBright™ Absolute Counting Beads were evaluated in each fluorescence histogram prior to each run to account for day-to-day instrument variations.

Figure 1P:
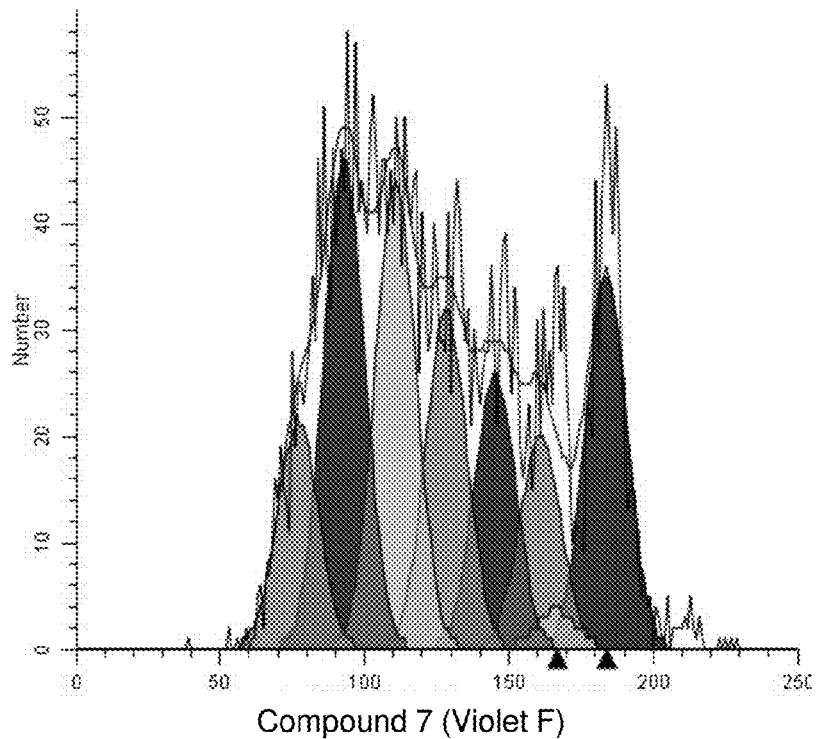

Results (Shown in FIGS. 1a-1p):

Proliferation was seen in cells stimulated with each of the three treatments (Concanavalin A, CD3/iL-2, and T cell expander beads). Unstimulated cells did not proliferate. CFSE displayed moderate fluorescence loss after the initial 24 hours. In contrast, Compound 2, Compound 6, and Compound 7 displayed very little loss of fluorescence over 24 hours. Each generation of cells was easily discernable by eye in the fluorescence histograms.

Example 2

Experimental Protocol:

Human peripheral blood mononuclear cells were isolated from whole blood using a Ficoll density gradient, then washed and resuspended in phosphate buffered saline (PBS) at a concentration of $10^6$/mL (see, Example 1). Two samples, one more recently synthesized than the other, of the cell-tracking compound Compound Violet were each dissolved in anhydrous dimethylsulfoxide to a final concentration of 5 mM. Two 4-mL aliquots of cells were stained with 4 µL of either Compound Violet sample for final staining concentrations of 1 µM. Cells were mixed by vortexing and incubated with agitation at room temperature for 20 minutes. Then 2 mL of heat-inactivated Fetal Bovine Serum were added, followed by 5 more minutes of incubation. Cells were then washed twice with PBS and resuspended in 4 mL of OpTmizer T-Cell Expansion Buffer (GIBCO) containing 2 mM L-glutamine, and 100,000 units penicillin and 100 mg streptomycin per liter. Aliquots (1 mL) of cells stained with each Compound Violet sample, and a 1-mL aliquot of unstained cells were then dispensed into a 12-well polystyrene plate and incubated at 37° C. and 5% $CO_2$ for 24 hours. One of the following four stimulus conditions were then applied individually to the cells: i) 200 ng anti-CD3 (2 µL), incubated on ice for 30 min, then transferred to culture plate and add 100 ng iL-2 per mL of culture media, ii) 5 µg/mL Concanavalin A (5 µL of a 1 mg/mL solution), iii) 75 µL CD3/CD28 T cell expander beads, or iv) no stimulus. The cells were then incubated for six more days at 37° C. and 5% $CO_2$. Aliquots (500 µL) of cells from each treatment were analyzed immediately following staining, and at 24 hours and six days after staining.

Sample Analysis:

An antibody cocktail containing 50 µl each of CD3 R-phycoerythrin, CD4 Alexa Fluor® 488, CD8 PE-Cy7, and CD19 Alexa Fluor® 647 is mixed. A 10-µl aliquot of this cocktail was added to 500-µL aliquots from each cell treatment for 15 minutes at room temperature. Cells were then washed and resuspended before adding 1 µL of SYTOX® AADvanced™ stain to each tube for 15 minutes at room temperature. Spectral compensation was calculated using single-color controls composed of stained AbC Anti-Mouse compensation beads for the antibodies, and heat killed cells for SYTOX® AADvanced™ stain. All samples were then run through the Becton Dickinson (BD™) LSR II Flow Cytometer. Fluorescence was collected using three lasers: the 405 nm excitation laser with 450/50 bandpass emission filter, the 488 nm excitation laser with 525/50, 585/42, 695/40, and 780/60 nm bandpass emission filters, and the 633 nm excitation laser with 660/20 nm bandpass emission filter. A gating strategy was employed to limit analysis to only the cells of interest. Cells were gated first on SYTOX® AADvanced™-stained negative (live) cells, then debris was gated out using the Forward Scatter/Side Scatter dot plot. T cells were differentiated from B cells using a CD3/CD19 dual parameter plot. T cells were further separated into CD4+ and CD8+ using another dual parameter plot. These cells were then displayed on a fluorescence histogram with 405 nm excitation and 450/50 nm emission.

Figure 2A:
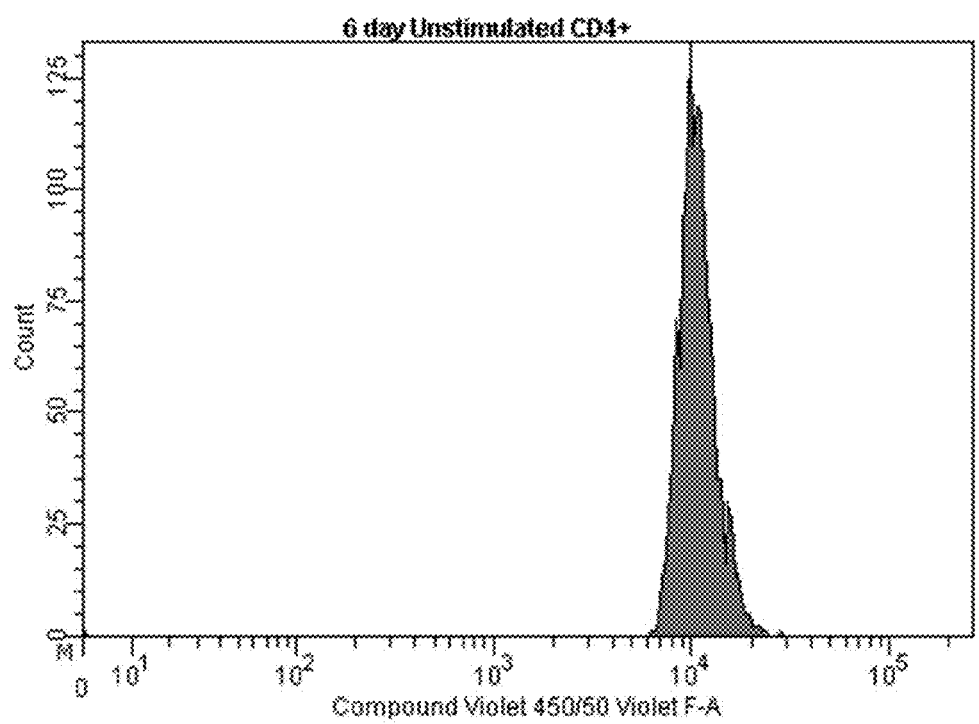
FIG. 2a-Unstimulated cells showing little change in fluorescence signal after six days of incubation with Compound Violet; the narrow fluorescence distribution and high mean fluorescence intensity shown in this plot are similar to those seen immediately after staining with Compound Violet.
Figure 2B:
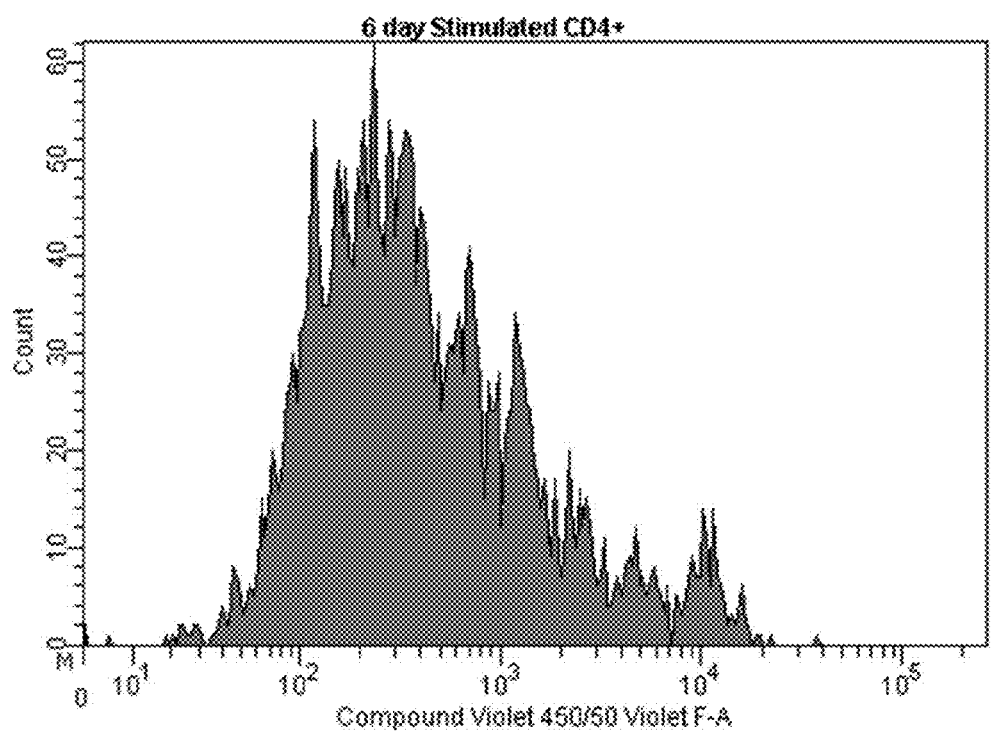
FIG. 2b-CD4 positive T cells proliferated rapidly when treated with CD3 and IL-2, as seen in this Compound Violet-generated fluorescence histogram. The fluorescence intensity of undivided cells is similar to that of the unstimulated control. The mean fluorescence intensity of each generation is approximately half that of the previous generation.

Results (Shown in FIGS. 2a-2b):

Proliferation was seen in cells stimulated with each of the three treatments (Concanavalin A, CD3/IL-2, and T cell expander beads). Unstimulated cells did not proliferate. CD4+ cells had the highest proliferation, with CD8+ cells proliferating less, and CD19+ B cells not appearing to proliferate at all. Compound Violet displayed very little loss of fluorescence over 24 hours. Each generation of cells was discernable by eye in the fluorescence histograms. Spectral compensation was easily performed for all six colors using cells and AbC antibody compensation beads.

Example 3

Experimental Protocol:

U2OS human osteosarcoma cells in complete media (McCoys media plus 10% FBS) were plated down at approximately 5000 cells/$cm^2$ and allowed to adhere to four MacTec dishes. Two dishes of cells were transfected with Cellular Lights™ Talin-GFP at a volume to volume of 10% for 24 hours prior to analysis. A 5 µM solution of Compound Violet was created by diluting 2 µL of 5 mM dye in anhydrous dimethylsulfoxide into 2 mL of phosphate buffered saline (PBS) containing calcium and magnesium. Growth medium was removed from two plates of cells and replaced with dye solution. Cells were stained at room temperature for 20 minutes and washed twice with PBS. Imaging analysis was performed on a Delta Vision microscope with filters for DAPI and FITC.

Figure 3A:
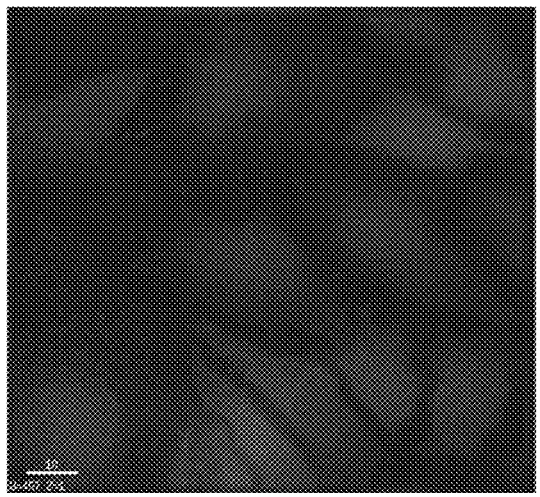
FIG. 3a-Cells stained with only Compound Violet showing bright blue fluorescence throughout the cytoplasm when viewed in the DAPI channel, but showing no fluorescence signal in the FITC channel.
Figure 3B:
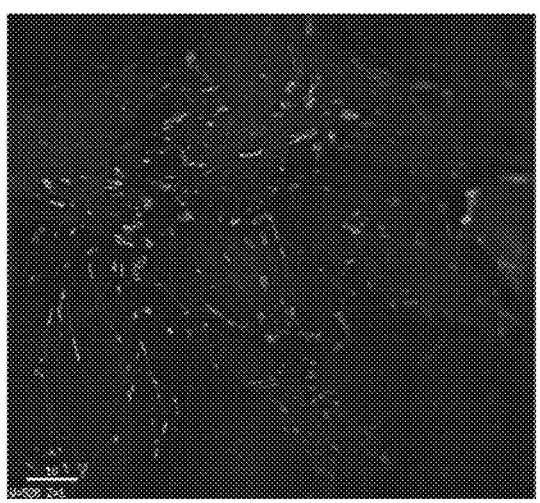
FIG. 3b-Cells transduced with Cellular Lights™ Talin-GFP showing punctate spots of bright green fluorescence in the cell periphery when viewed in the FITC channel, but no fluorescence signal when viewed in the DAPI channel.
Figure 3C:
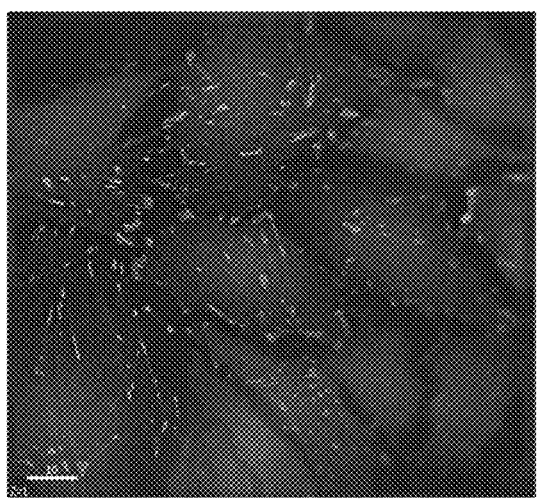
FIG. 3c-Cells transduced with Cellular Lights™ Talin-GFP and stained with Compound Violet showing bright blue fluorescence throughout the cytoplasm and punctate green fluorescence in the cell perimeter.
Figure 4A:
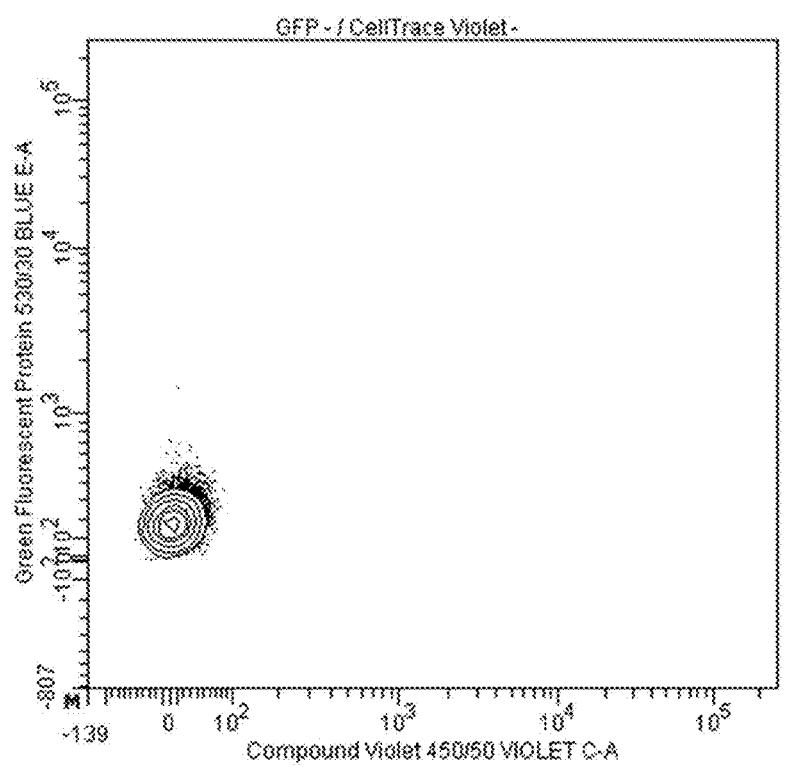
FIG. 4a-Unstained cells with no GFP expression showing very little fluorescence in either channel.
Figure 4B:
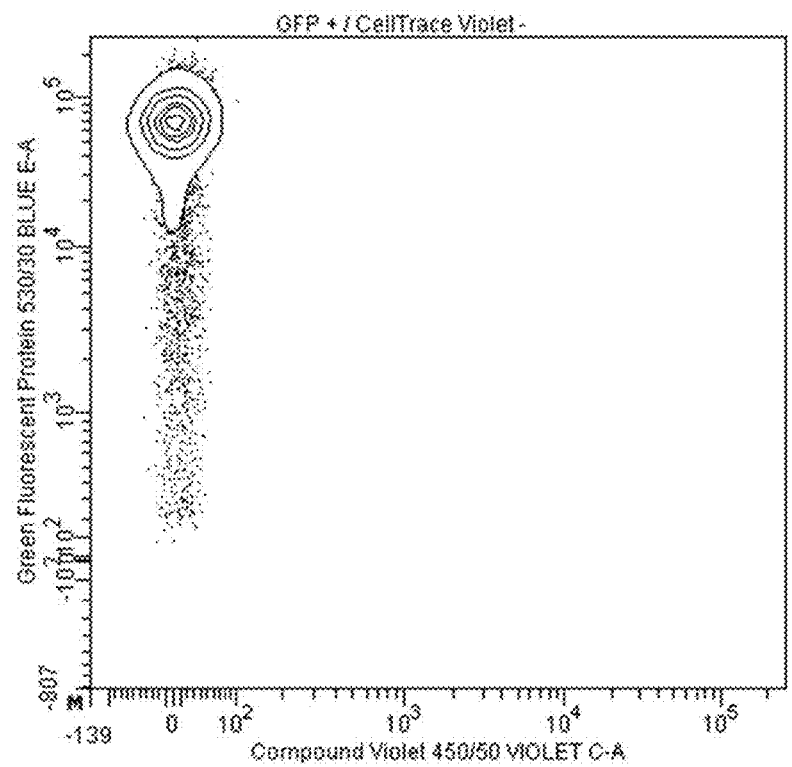
FIG. 4b-Unstained cells expressing GFP showing bright fluorescence in the blue 525/50 channel, but very little signal in the violet 450/50 channel.
Figure 4C:
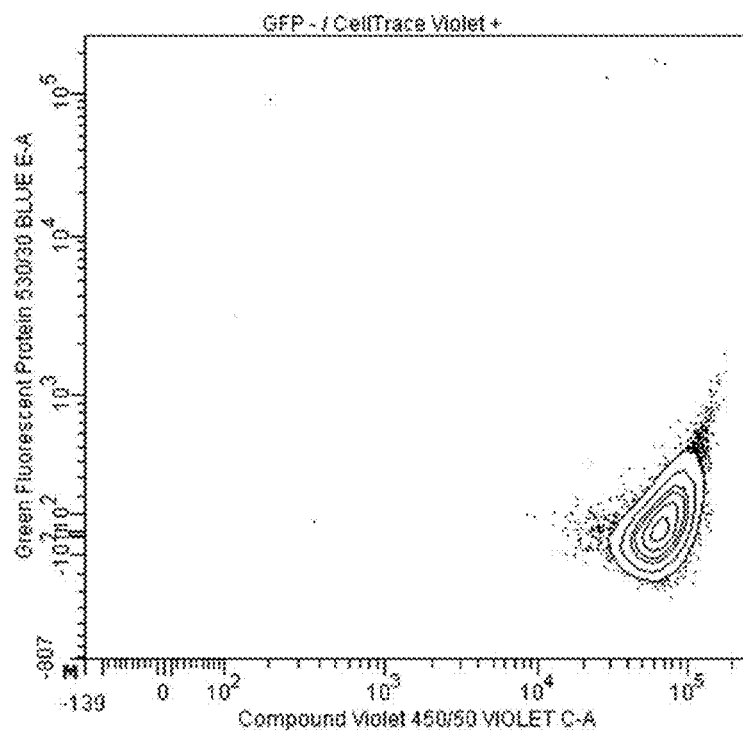
FIG. 4c-Cells stained with Compound Violet with no GFP expression showing bright fluorescence in the violet 450/50 channel, but very little signal in the blue 525/50 channel.
Figure 4D:
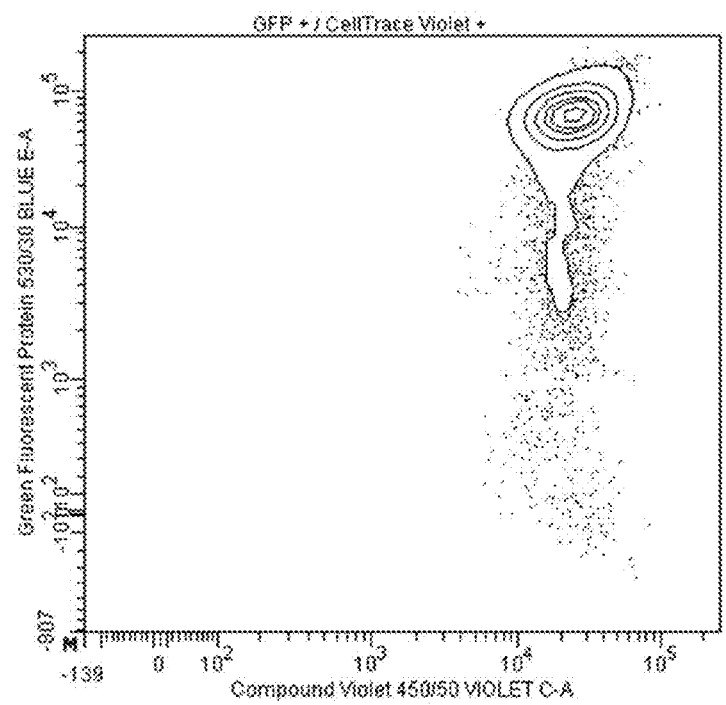
FIG. 4d-Cell expressing GFP and stained with Compound Violet showing bright fluorescence in both channels; these results indicate that GFP and Compound Violet can be used simultaneously, without adverse spectral interactions.
Figure 5A:
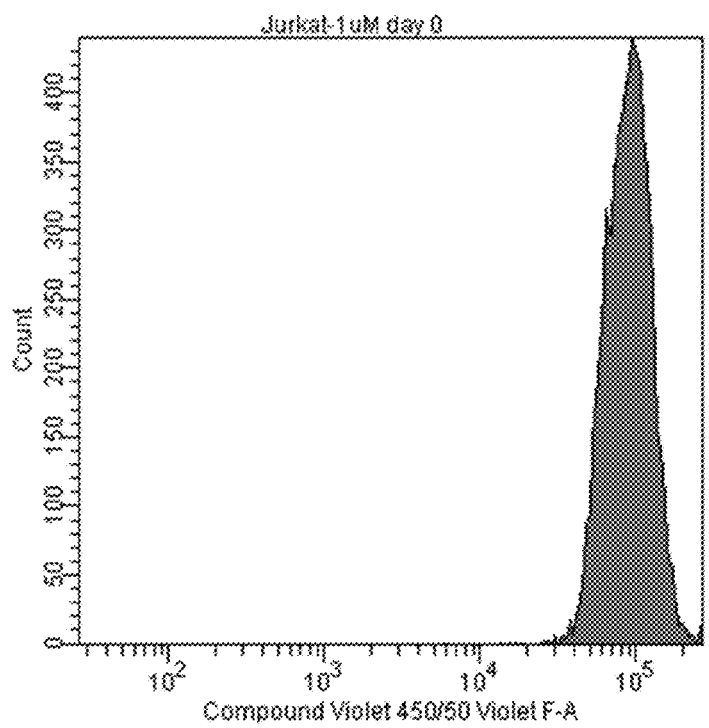
FIG. 5a-Jurkat cells stained with 1 μM Compound Violet showing a bright, uniform fluorescence signal immediately after staining.
Figure 5B:
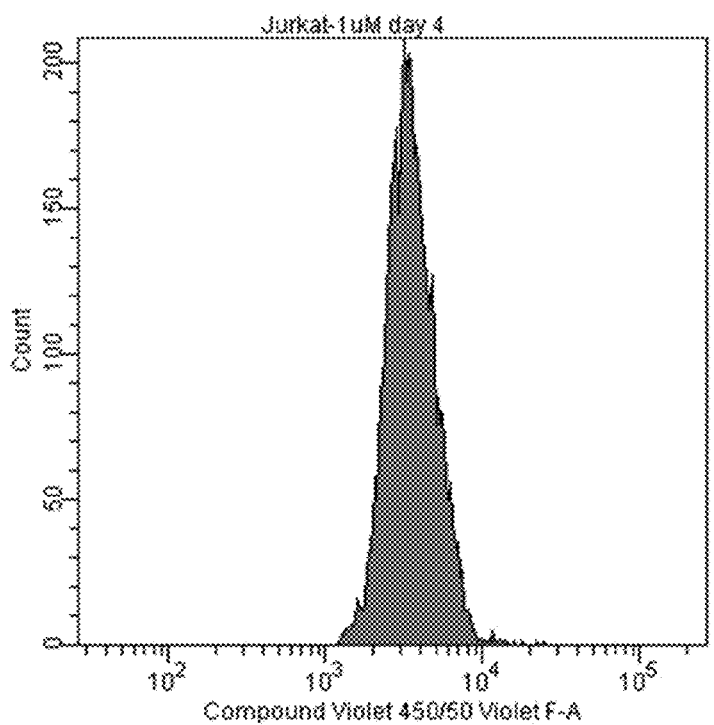
FIG. 5b-Jurkat cells stained with 1 μM Compound Violet showing that the fluorescence signal has decreased substantially after four days of cell division in culture.
Figure 5C:
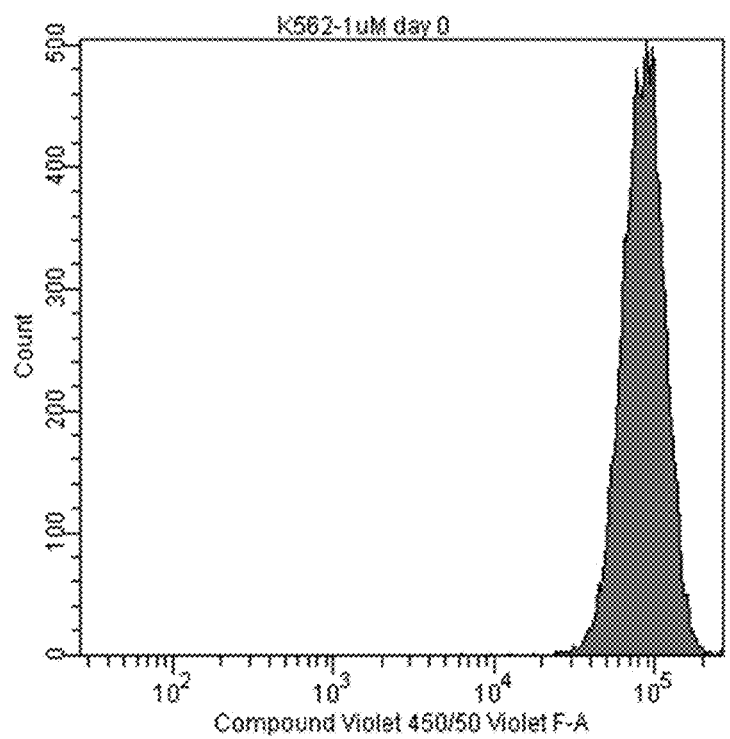
FIG. 5c-K562 cells stained with 1 μM Compound Violet showing a bright, uniform fluorescence signal immediately after staining.
Figure 5D:
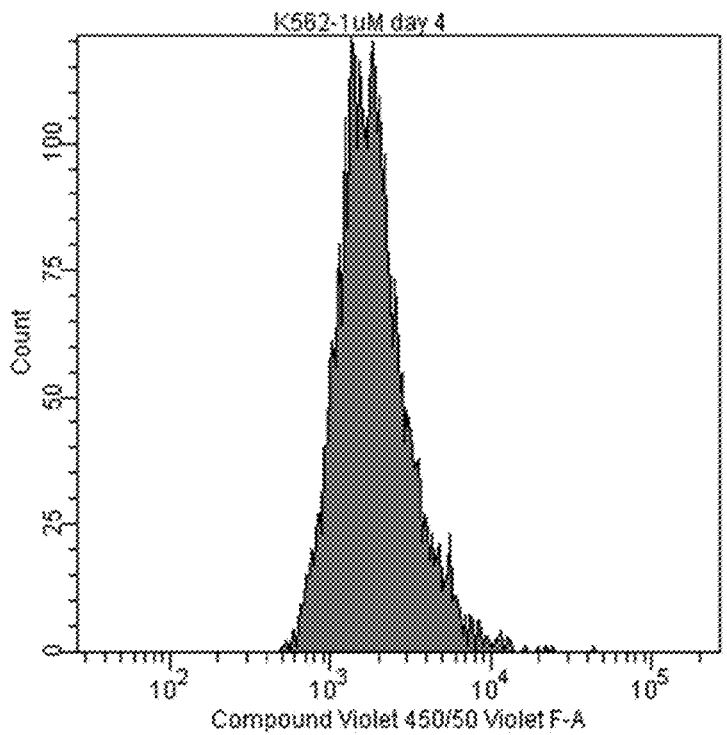
FIG. 5d-K562 cells stained with 1 μM Compound Violet showing that the fluorescence signal has decreased substantially after four days of cell division in culture.
Figure 5E:
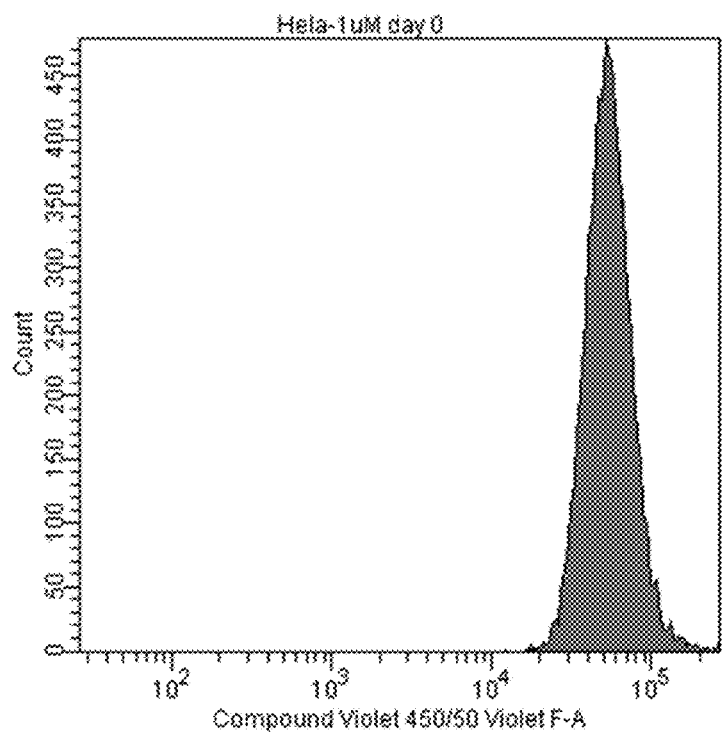
FIG. 5e-Hela cells stained with 1 μM Compound Violet showing a bright, uniform fluorescence signal immediately after staining.
Figure 5F:
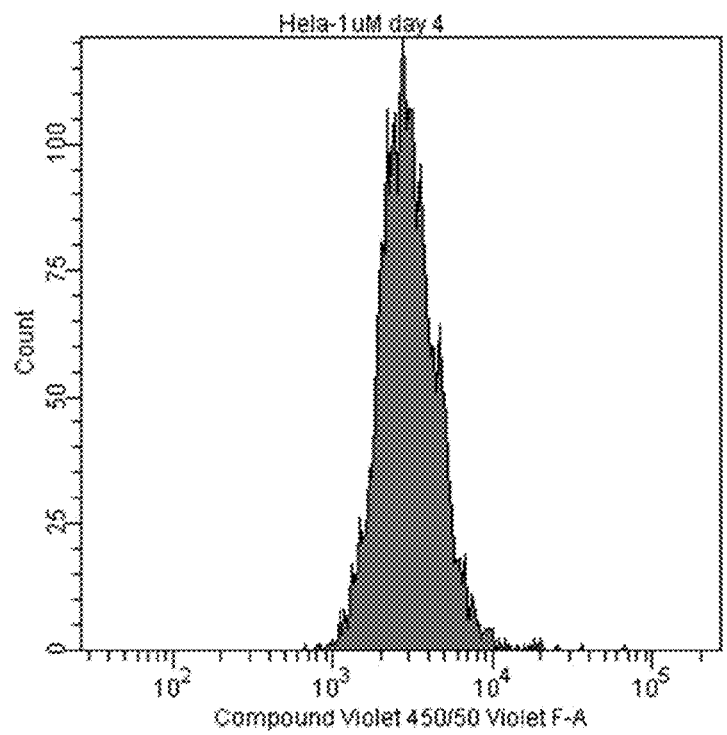
FIG. 5f-Hela cells stained with 1 μM Compound Violet showing that the fluorescence signal has decreased substantially after four days of cell division in culture.
Figure 5G:
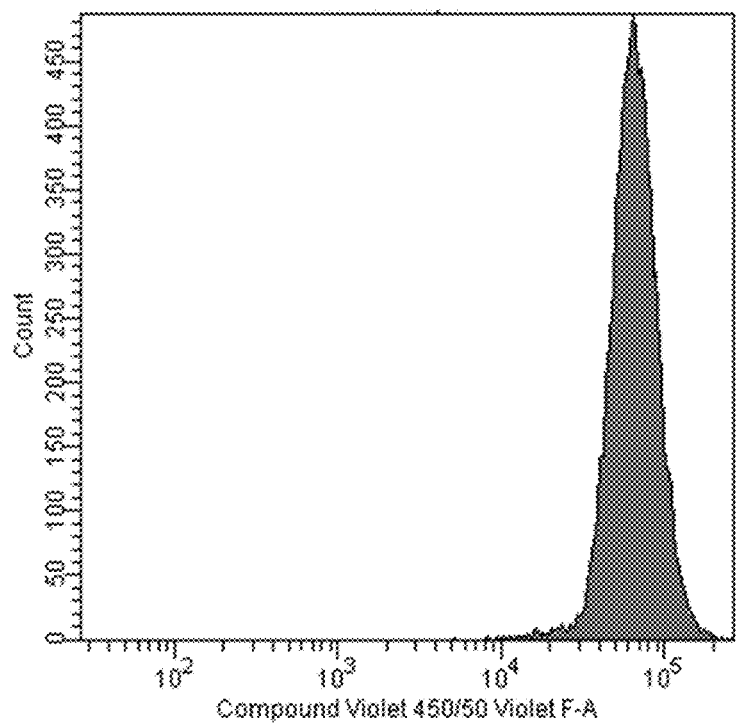
Figure 5H:
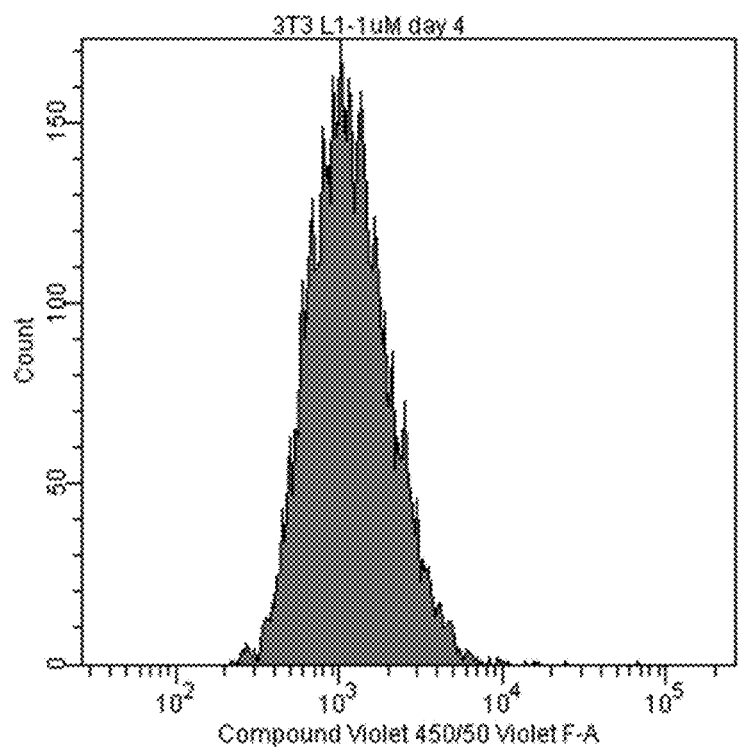
Figure 6:
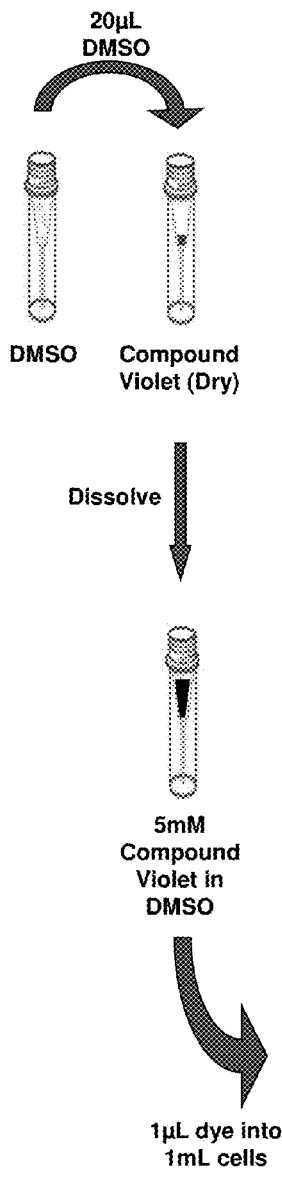
FIG. 6 shows a proposed experimental protocol for use of a Compound Violet cell proliferation kit.
Figure 7:
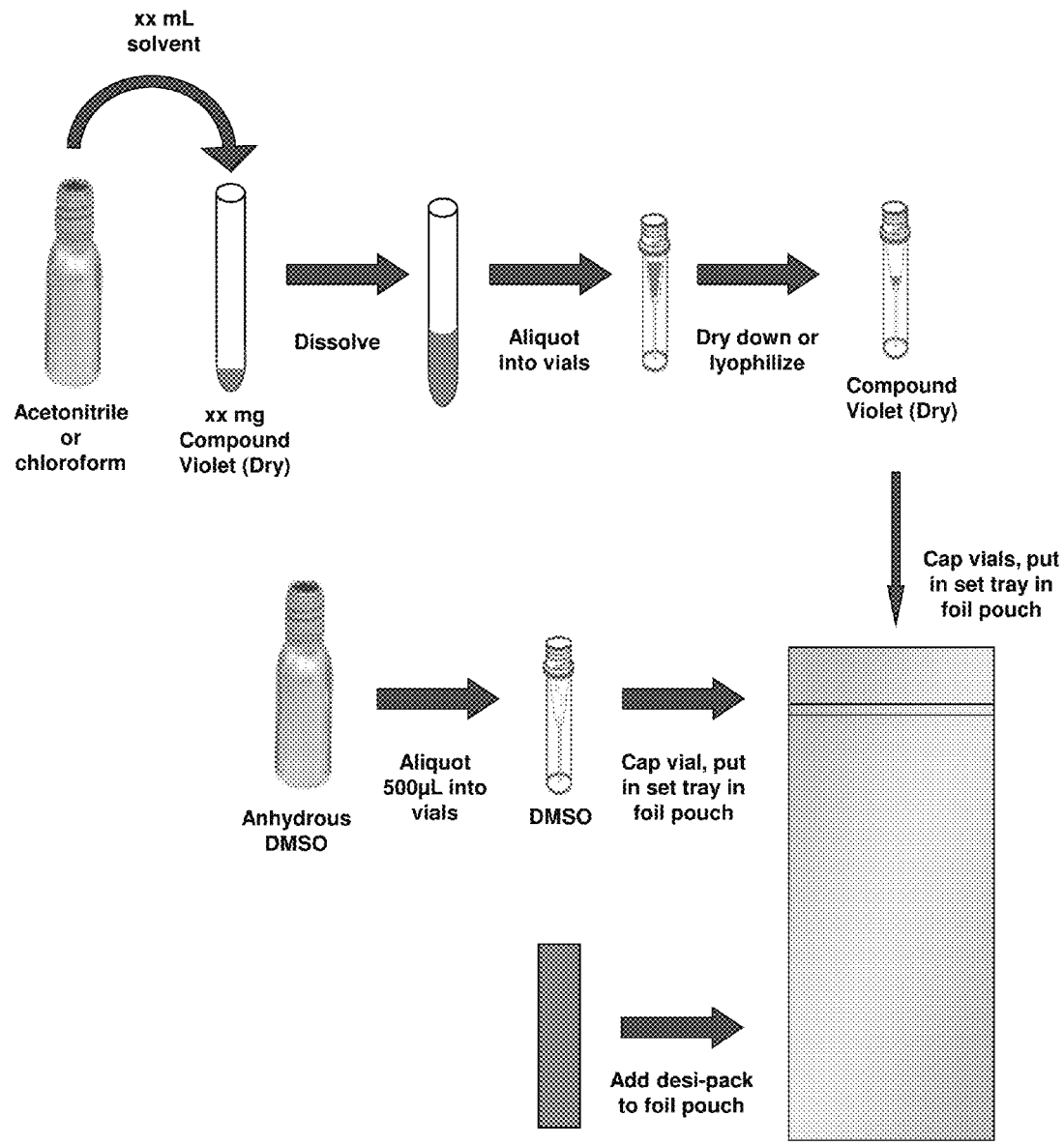
FIG. 7 shows a proposed packaging protocol for a Compound Violet cell proliferation kit.

Results (Shown in FIGS. 3a-3c):

Compound Violet and GFP each appeared brightly fluorescent in their respective emission filters, and there did not appear to be fluorescence overlap into the opposite emission filters.

Example 4

Experimental Protocol:

Flasks of two cell lines, MCF7 (stably expressing Green Fluorescent Protein, GFP) and U2OS (no fluorescent protein expression), were trypsinized and suspended in phosphate buffered saline (PBS) at a concentration of $10^6$ cells/mL. Each cell type was divided into equal aliquots, with one aliquot left unstained and the other stained with 5 µM Compound Violet (prepared as described in Example 3) for 20 minutes at room temperature. Cells were then analyzed on the Becton Dickinson (BD) LSRII Flow Cytometer. Fluorescence was collected using two lasers: the 405 nm excitation laser with 450/50 bandpass emission filter and the 488 nm excitation laser with 525/50 bandpass emission filter.

Results (Shown in FIGS. 4a-4d):

Unstained cells with no GFP expression showed very little fluorescence in either channel. Unstained cells expressing GFP displayed bright fluorescence in the blue 525/50 channel, but very little signal in the violet 450/50 channel. Stained cells with no GFP expression displayed bright fluorescence in the violet 450/50 channel, but very little signal in the blue 525/50 channel. Cells expressing GFP and stained with Compound Violet displayed bright fluorescence in both channels. These results indicate that GFP and Compound Violet can be used simultaneously, without adverse spectral interactions.

Example 5

Experimental Protocol:

Four different cell lines (Jurkat, K562, Hela, and 3T3-L1) were harvested and resuspended in phosphate buffered saline (PBS) at a concentration of $5 \times 10^5$ cells per milliliter. Aliquots (1 mL) of each cell type were stained with 1 µL of 1 mM Compound Violet in anhydrous dimethylsulfoxide for 20 minutes at room temperature. Cells were then washed twice with RPMI media containing 10% fetal bovine serum and stained with 1 µM SYTOX® Red Dead Cell Stain for 10 minutes at room temperature. Cells were analyzed on a BD LSRII flow cytometer using a 405 nm laser with 450/50 bandpass emission filter and a 635 nm laser with 660/20 bandpass emission filter. Analysis was performed immediately after staining and repeated after cells were grown in culture (37° C., 5% $CO_2$) for 96 hours. Compound Violet fluorescence was analyzed in live cells using a gate on cells that did not take up SYTOX® Red Dead Cell Stain.

Results (Shown in FIGS. 5a-5h):

Good staining was observed in all cell lines tested. All Jurkats seemed to be in the same generation, while other cell lines seemed to model 2-3 generations.

Prophetic Biological Application Examples of Cell-Tracking Reagents (Compounds)

It is anticipated that, in addition to the in vitro flow cytometry cell-tracking applications and the fluorescence microscopy cytoplasmic counterstain application described above, the cell-tracking reagents (compounds) of the present invention, including Compound Violet, will also find application in vivo to stain cells and track their migration, location, and/or proliferation in a manner similar to that already established for CFDA-SE and as described, for example, by Lyons et al. (see, Lyons A B, Doherty K V. Flow Cytometric Analysis of Cell Division by Dye Dilution. *Current Protocols in Cytometry,* 2004, 9.11.1-9.11.10). It is further anticipated that the cell-tracking reagents (compounds) of the present invention, including Compound Violet, will also find application in clinical research models related to adoptive transfer in transplantation, GVHD, cell-mediated therapies and research.

Each of the above-cited references and all methods disclosed therein are hereby incorporated herein by reference as if set forth fully herein.

The invention claimed is:

1. A compound of structural formula:

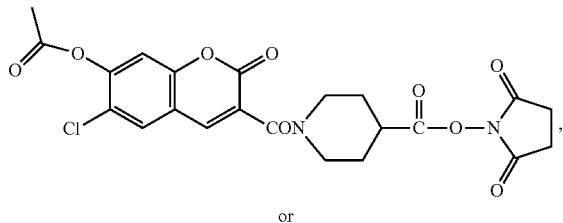

or

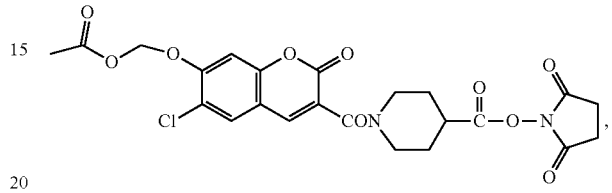

or a pharmaceutically acceptable salt thereof.

2. A kit for tracking cell proliferation, differentiation, and/or function, the kit comprising:

a) a compound of structural formula:

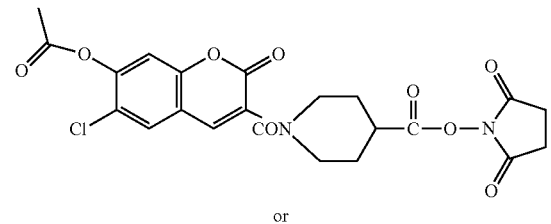

or

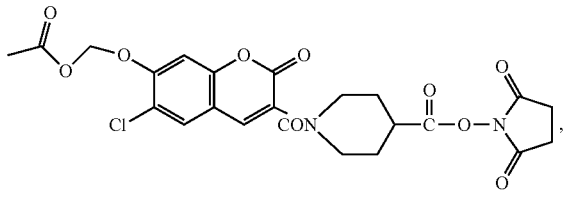

or a pharmaceutically acceptable salt thereof;
b) an organic solvent; and
c) a desiccant.

3. The kit according to claim 2, wherein the compound is excitable with a 405-nm violet laser.

4. The compound of claim 1, wherein the compound diffuses into one or more cells and is retained within the one or more cells for multiple generations of the one or more cells.

5. The compound of claim 1, wherein the compound diffuses into one or more cell and is retained within the one or more cell for at least 6 days.

6. The compound of claim 1, wherein the compound diffuses into one or more cell and does not lose fluorescence intensity after 24 hours.

* * * * *